US008992416B2

(12) United States Patent
Mandava et al.

(10) Patent No.: US 8,992,416 B2
(45) Date of Patent: Mar. 31, 2015

(54) ENDOSCOPE STORAGE CABINET, TRACKING SYSTEM, AND SIGNAL EMITTING MEMBER

(71) Applicant: Mobile Aspects, Inc., Pittsburgh, PA (US)

(72) Inventors: Suneil Mandava, Pittsburgh, PA (US); Timur P. Sriharto, Monroeville, PA (US); Gino N. Iasella, Gibsonia, PA (US); Khang Nguyen Le, Pittsburgh, PA (US); Pribadi Kardono, Monroeville, PA (US); Hansen Brenkus, Penn, PA (US); Muhammad R. Rahim, Monroeville, PA (US); Jared Kiah Frye, Cranberry, PA (US); Prasad Venkata Lakshmi Mandava, Bangalore (IN); Balaji Rengeswamy, Bangalore (IN)

(73) Assignee: Mobile Aspects, Inc., Pittsburgh, PA (US)

( * ) Notice: Subject to any disclaimer, the term of this patent is extended or adjusted under 35 U.S.C. 154(b) by 0 days.

(21) Appl. No.: 13/793,201

(22) Filed: Mar. 11, 2013

(65) Prior Publication Data

US 2014/0097954 A1   Apr. 10, 2014

Related U.S. Application Data

(63) Continuation of application No. 12/607,732, filed on Oct. 28, 2009, now Pat. No. 8,414,471.

(60) Provisional application No. 61/108,945, filed on Oct. 28, 2008.

(51) Int. Cl.
| | |
|---|---|
| *A61B 1/00* | (2006.01) |
| *G08B 13/14* | (2006.01) |
| *A61B 19/02* | (2006.01) |
| *G06K 7/10* | (2006.01) |

(Continued)

(52) U.S. Cl.
CPC ........ *A61B 19/0248* (2013.01); *G06K 7/10405* (2013.01); *G08B 5/36* (2013.01); *H01Q 17/00* (2013.01); *A61B 2019/0249* (2013.01); *A61B 2019/448* (2013.01)
USPC ....................................... 600/101; 340/572.1

(58) Field of Classification Search
USPC ........................... 455/95; 340/572.1; 600/101
See application file for complete search history.

(56) References Cited

U.S. PATENT DOCUMENTS

| | | | |
|---|---|---|---|
| 3,958,102 | A | 5/1976 | Burt |
| 4,116,512 | A | 9/1978 | Wiser |

(Continued)

FOREIGN PATENT DOCUMENTS

| | | | |
|---|---|---|---|
| JP | 2001052054 A | 2/2001 | |
| JP | 2002282200 A | 10/2002 | |

OTHER PUBLICATIONS

U.S. Appl. No. 14/013,625, filed Aug. 29, 2013.
U.S. Appl. No. 12/240,022, filed Sep. 29, 2008.
U.S. Appl. No. 13/662,897, filed Oct. 29, 2012.

*Primary Examiner* — W B Perkey
(74) *Attorney, Agent, or Firm* — The Webb Law Firm

(57) ABSTRACT

An endoscope storage cabinet for use with at least one endoscope having at least one signal emitting member associated therewith and configured to emit a signal indicative of at least one attribute of the at least one endoscope to which it is associated, the cabinet including: an enclosed structure formed by a plurality of walls defining an inner area which is accessible by at least one door; at least one hanger arrangement configured to support at least a portion of at least one endoscope positioned thereon; at least one signal receiving device associated with the enclosed structure and configured to receive the signal emitted by the at least one signal emitting member; and a local control device in communication with the at least one signal receiving device and configured to receive and process the signal emitted by the at least one signal emitting member.

17 Claims, 18 Drawing Sheets

(51) Int. Cl.
  *G08B 5/36* (2006.01)
  *H01Q 17/00* (2006.01)
  *A61B 19/00* (2006.01)

(56) References Cited

U.S. PATENT DOCUMENTS

| | | | |
|---|---|---|---|
| 4,118,693 A | 10/1978 | Novikoff | |
| 4,227,037 A | 10/1980 | Layton | |
| 4,496,406 A | 1/1985 | Dedow | |
| 4,636,634 A | 1/1987 | Harper et al. | |
| 4,636,950 A | 1/1987 | Caswell et al. | |
| 4,673,932 A | 6/1987 | Ekchian et al. | |
| 4,847,764 A | 7/1989 | Halvorson | |
| 4,860,918 A | 8/1989 | Wuyten et al. | |
| 5,029,183 A | 7/1991 | Tymes | |
| 5,194,856 A | 3/1993 | Zijlstra | |
| 5,287,414 A | 2/1994 | Foster | |
| 5,295,154 A | 3/1994 | Meier et al. | |
| 5,389,919 A | 2/1995 | Warren et al. | |
| 5,408,443 A | 4/1995 | Weinberger | |
| 5,410,315 A | 4/1995 | Huber | |
| 5,413,236 A | 5/1995 | Kenevan | |
| 5,431,299 A | 7/1995 | Brewer et al. | |
| 5,495,961 A | 3/1996 | Maestre | |
| 5,565,858 A | 10/1996 | Guthrie | |
| 5,689,238 A | 11/1997 | Cannon, Jr. et al. | |
| 5,713,485 A | 2/1998 | Liff et al. | |
| 5,729,697 A | 3/1998 | Schkolnick et al. | |
| 5,739,765 A | 4/1998 | Stanfield et al. | |
| 5,751,220 A | 5/1998 | Ghaffari | |
| 5,751,221 A | 5/1998 | Stanfield et al. | |
| 5,765,707 A | 6/1998 | Kenevan | |
| 5,771,003 A | 6/1998 | Seymour | |
| 5,774,053 A | 6/1998 | Porter | |
| 5,774,059 A | 6/1998 | Henry et al. | |
| 5,797,515 A | 8/1998 | Liff et al. | |
| 5,801,628 A | 9/1998 | Maloney | |
| 5,804,810 A | 9/1998 | Woolley et al. | |
| 5,857,152 A | 1/1999 | Everett | |
| 5,912,818 A | 6/1999 | McGrady et al. | |
| 5,917,433 A | 6/1999 | Keillor et al. | |
| 5,936,527 A | 8/1999 | Isaacman et al. | |
| 5,950,630 A | 9/1999 | Portwood et al. | |
| 5,993,046 A | 11/1999 | McGrady et al. | |
| 6,075,441 A | 6/2000 | Maloney | |
| 6,112,502 A | 9/2000 | Frederick et al. | |
| 6,116,461 A | 9/2000 | Broadfield et al. | |
| 6,127,928 A | 10/2000 | Issacman et al. | |
| 6,204,764 B1 | 3/2001 | Maloney | |
| 6,296,148 B1 | 10/2001 | Myers et al. | |
| 6,323,782 B1 | 11/2001 | Stephens et al. | |
| 6,392,544 B1 | 5/2002 | Collins et al. | |
| 6,407,665 B2 | 6/2002 | Maloney | |
| 6,424,262 B2 | 7/2002 | Garber et al. | |
| 6,445,297 B1 | 9/2002 | Nicholson | |
| 6,512,459 B2 | 1/2003 | Benezech et al. | |
| 6,512,478 B1 | 1/2003 | Chien | |
| 6,677,857 B2 | 1/2004 | Bara et al. | |
| 6,703,935 B1 | 3/2004 | Chung et al. | |
| 6,707,381 B1 | 3/2004 | Maloney | |
| 6,714,121 B1 | 3/2004 | Moore | |
| 6,718,888 B2 | 4/2004 | Muirhead | |
| 6,745,027 B2 | 6/2004 | Twitchell, Jr. | |
| 6,747,558 B1 | 6/2004 | Thorne et al. | |
| 6,750,771 B1 | 6/2004 | Brand | |
| 6,762,676 B2 | 7/2004 | Teowee et al. | |
| 6,826,514 B1 | 11/2004 | Antico et al. | |
| 6,870,464 B2 | 3/2005 | Okamura | |
| 6,943,678 B2 | 9/2005 | Muirhead | |
| 6,989,749 B2 | 1/2006 | Mohr | |
| 7,009,518 B2 | 3/2006 | Liao et al. | |
| 7,009,576 B2 * | 3/2006 | Adamson et al. | 343/873 |
| 7,126,926 B1 | 10/2006 | Bjorklund et al. | |
| 7,130,773 B1 | 10/2006 | Wong | |
| 7,135,973 B2 * | 11/2006 | Kittel et al. | 340/568.2 |
| 7,152,791 B2 | 12/2006 | Chappidi et al. | |
| 7,187,287 B2 | 3/2007 | Ryal | |
| 7,233,620 B2 | 6/2007 | Brommer | |
| 7,256,682 B2 | 8/2007 | Sweeney, II | |
| 7,265,675 B1 | 9/2007 | Carrender et al. | |
| 7,286,043 B2 | 10/2007 | Carrender et al. | |
| 7,298,243 B2 | 11/2007 | Juels et al. | |
| 7,310,045 B2 | 12/2007 | Inui | |
| 7,318,261 B2 * | 1/2008 | Bills | 27/1 |
| 7,342,496 B2 | 3/2008 | Muirhead | |
| 7,348,884 B2 | 3/2008 | Higham | |
| 7,401,375 B2 * | 7/2008 | McLeod | 15/104.002 |
| 7,420,458 B1 | 9/2008 | Kuzma et al. | |
| 7,433,648 B2 | 10/2008 | Bridgelall | |
| 7,758,523 B2 * | 7/2010 | Collings et al. | 600/592 |
| 8,120,497 B2 * | 2/2012 | Binmore | 340/572.8 |
| 2001/0002448 A1 | 5/2001 | Wilson et al. | |
| 2001/0028308 A1 | 10/2001 | De La Huerga | |
| 2001/0034613 A1 | 10/2001 | Rubsamen | |
| 2001/0044731 A1 | 11/2001 | Coffman et al. | |
| 2001/0052054 A1 | 12/2001 | Franke et al. | |
| 2002/0027507 A1 | 3/2002 | Yarin et al. | |
| 2002/0038167 A1 | 3/2002 | Chirnomas | |
| 2002/0063622 A1 | 5/2002 | Armstrong et al. | |
| 2002/0113082 A1 | 8/2002 | Leatherman et al. | |
| 2002/0143320 A1 | 10/2002 | Levin | |
| 2002/0145520 A1 | 10/2002 | Maloney | |
| 2002/0153411 A1 | 10/2002 | Wan et al. | |
| 2002/0183882 A1 | 12/2002 | Dearing et al. | |
| 2002/0190871 A1 | 12/2002 | Stanfield et al. | |
| 2003/0030539 A1 | 2/2003 | McGarry et al. | |
| 2003/0034390 A1 | 2/2003 | Linton et al. | |
| 2003/0117281 A1 | 6/2003 | Sriharto | |
| 2003/0160698 A1 | 8/2003 | Andreasson et al. | |
| 2003/0164401 A1 | 9/2003 | Andreasson et al. | |
| 2003/0174099 A1 | 9/2003 | Bauer et al. | |
| 2004/0046020 A1 | 3/2004 | Andreasson et al. | |
| 2004/0069850 A1 | 4/2004 | De Wilde | |
| 2004/0069852 A1 | 4/2004 | Seppinen et al. | |
| 2004/0111335 A1 | 6/2004 | Black et al. | |
| 2004/0155003 A1 | 8/2004 | Anderson et al. | |
| 2004/0168618 A1 | 9/2004 | Muirhead | |
| 2004/0267545 A1 | 12/2004 | Buchmann et al. | |
| 2005/0024211 A1 | 2/2005 | Maloney | |
| 2005/0088284 A1 | 4/2005 | Zai et al. | |
| 2005/0088305 A1 | 4/2005 | Greene et al. | |
| 2005/0093679 A1 | 5/2005 | Zai et al. | |
| 2005/0099283 A1 * | 5/2005 | Johnson et al. | 340/447 |
| 2005/0237184 A1 | 10/2005 | Muirhead | |
| 2005/0241548 A1 | 11/2005 | Muirhead | |
| 2005/0280539 A1 | 12/2005 | Pettus | |
| 2006/0022800 A1 | 2/2006 | Krishna et al. | |
| 2006/0028081 A1 | 2/2006 | Minagawa | |
| 2006/0056370 A1 | 3/2006 | Hancock et al. | |
| 2006/0058018 A1 | 3/2006 | Toulis et al. | |
| 2006/0092040 A1 | 5/2006 | Fishkin et al. | |
| 2006/0109084 A1 | 5/2006 | Yarvis | |
| 2006/0143439 A1 | 6/2006 | Arumugam et al. | |
| 2006/0187043 A1 | 8/2006 | Allen | |
| 2006/0215593 A1 | 9/2006 | Wang et al. | |
| 2007/0046467 A1 | 3/2007 | Chakraborty et al. | |
| 2007/0096876 A1 | 5/2007 | Bridgelall et al. | |
| 2007/0103303 A1 | 5/2007 | Shoarinejad | |
| 2007/0164109 A1 | 7/2007 | Ridings et al. | |
| 2007/0171992 A1 | 7/2007 | Shameli et al. | |
| 2007/0172007 A1 | 7/2007 | Shoarinejad et al. | |
| 2007/0188342 A1 | 8/2007 | Valeriano et al. | |
| 2007/0200724 A1 | 8/2007 | Lazo et al. | |
| 2007/0216534 A1 * | 9/2007 | Ferguson et al. | 340/572.7 |
| 2007/0279202 A1 * | 12/2007 | Lionetti | 340/447 |
| 2008/0061940 A1 | 3/2008 | Onderko et al. | |
| 2008/0117050 A1 | 5/2008 | Wu et al. | |
| 2008/0198016 A1 | 8/2008 | Lawrence et al. | |
| 2008/0218354 A1 | 9/2008 | Lorentz et al. | |
| 2009/0009332 A1 * | 1/2009 | Nunez et al. | 340/572.1 |
| 2009/0261956 A1 | 10/2009 | Ojeda et al. | |

* cited by examiner

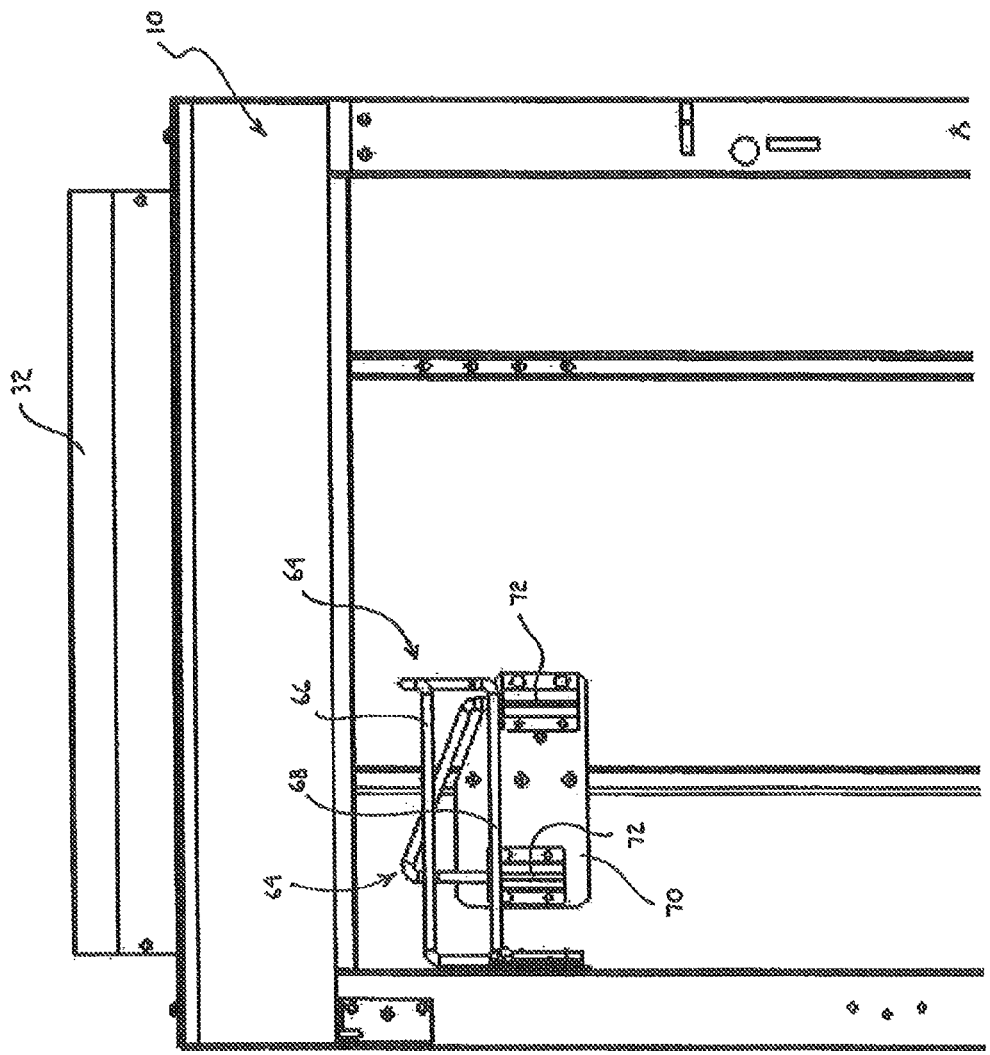

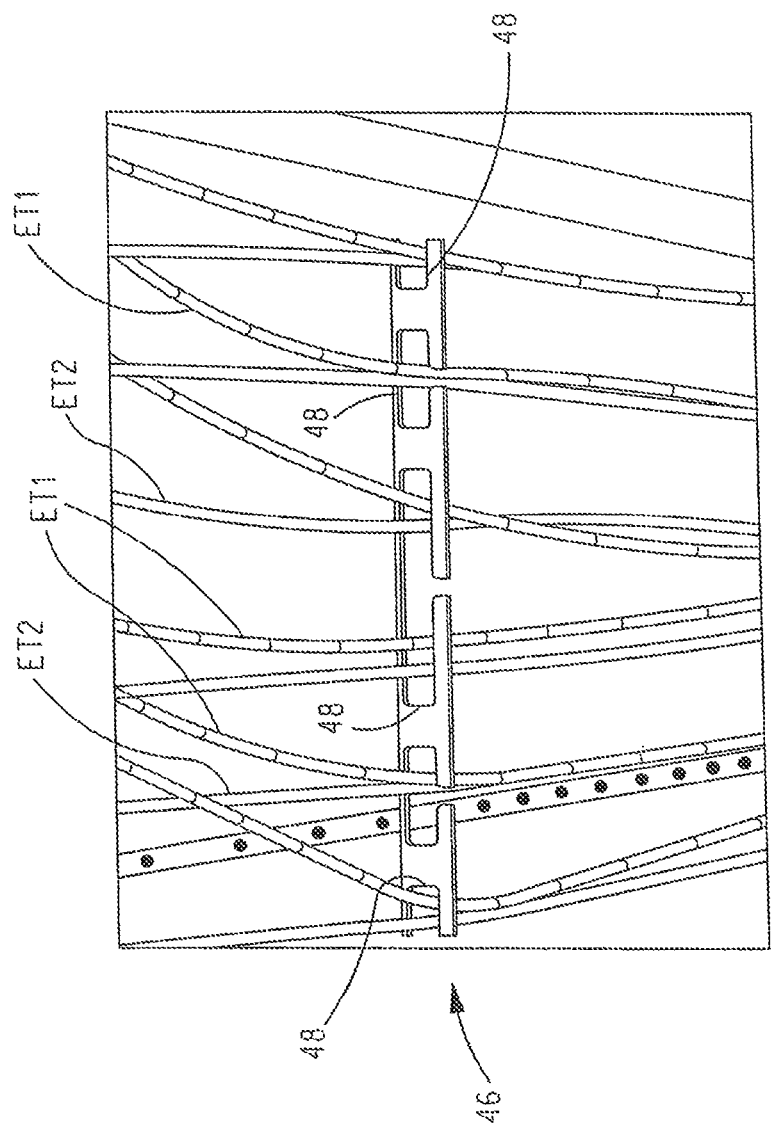

ENDOSCOPE STORAGE CABINET, TRACKING SYSTEM, AND SIGNAL EMITTING MEMBER

CROSS REFERENCE TO RELATED APPLICATIONS

This application is a continuation application of U.S. application Ser. No. 12/607,732, filed Oct. 28, 2009, which claims the benefit of priority of U.S. Provisional Patent Application No. 61/108,945, filed Oct. 28, 2008, which is incorporated herein by reference in its entirety.

BACKGROUND OF THE INVENTION

1. Field of the Invention

The present invention relates generally to medical device storage arrangements, inventory management methods and systems, and signal emitting members, such as radio frequency identification tags, systems, and the like. In particular, the present invention relates to an endoscope storage cabinet, a tracking method and system for use in connection with endoscopes and the like, and an improved signal emitting member.

2. Description of the Related Art

Presently, in the health care industry, complex and expensive equipment and systems are utilized in the diagnosis and care process. As the development of this equipment and associated systems continues, the necessity to monitor and track the usage is of the utmost importance. Certain drawbacks and deficiencies exist in the prior art, including: (1) theft of the equipment or its components; (2) inaccurate manual compliance and tracking methods; (3) ineffective and inefficient compliance monitoring and similar management; (4) inefficient equipment sharing and distribution; (5) high repair costs; (6) difficulty in tracking; (7) inaccurate identification and tracking methods, etc.

Many medical devices, such as an endoscope, represent a highly complex and expensive medical instrument to purchase, maintain and repair. Unfortunately, equipment theft does occur, with some hospitals reporting the loss of 5-7 endoscopes, which, as stated, are extremely expensive to replace. According to the prior art, and especially in those procedures involving the use of an endoscope, compliance with hospital protocol is an entirely manual process, i.e., using "pen and paper."

Further, endoscopes are currently being stored in unlocked cabinets, which are often left open, and in some cases, positioned in the middle of a high-traffic hallway. This represents a contamination issue, a potential damage issue, a potential theft/loss issue, a tracking issue, etc. According to the prior art, endoscopes are routinely returned from procedure rooms if not used during the procedure, and simply re-hung in the cabinet. However, there exists no control in place to prevent "dirty" endoscopes from potentially cross-contaminating the entire cabinet.

In addition, compliance monitoring, decontamination (cleaning) and disinfection protocols are entirely manual, and time-based measures of workforce efficiencies are virtually nonexistent. Another issue arises when endoscopes are borrowed by other departments, and are subsequently lost or misplaced. Accordingly, such endoscopes are not available when required by the appropriate personnel. In addition, the hospitals must then assign individuals to spend time locating these expensive instruments. Since the sign-out procedures are normally manual, users may forget to sign-out the equipment according to the procedure.

The repair costs associated with an endoscope is very high, and on some occasions, individual endoscopes can be "lemons" and require additional repair (with the associated costs). Some doctors report damage often, which will trigger excessive repair costs. Presently, there is no way of tracing if a specific individual is the common factor in multiple damage endoscopes. Still further, there is no effective process to identify and track loaner scopes, and little data is available to the managers of any "Continuous Improvement" process, i.e., there is no way of knowing if an endoscope scope has been lost. Presently, recordkeeping directed to these endoscopes is manual and time-intensive.

Preventive maintenance of these endoscopes is often ad-hoc at times, and existing systems are often not integrated into the process to manage and tune preventative maintenance cycles and activities. Additionally, while endoscopes do have individual and unique serial numbers, trying to locate this number amongst a tangled jumble of insertion tubes and umbilical cables is extremely difficult, and since endoscope pools are not load-rotated, the scopes in front get used more often, etc.

Accordingly, such prior art storage, tracking, and inventory management systems are ineffective and/or inefficient in monitoring, tracking and communicating information directed to specified equipment, e.g., an endoscope or the like.

SUMMARY OF THE INVENTION

The present invention provides an endoscope storage cabinet, tracking system, and signal emitting member that overcomes some or all of the above-noted drawbacks and deficiencies. Preferably, the present invention provides an endoscope storage cabinet that provides secure storage and tracking of one or more endoscopes. Preferably, the present invention provides an endoscope tracking system that tracks, analyzes, and controls the data associated with each unique endoscope. Preferably, the present invention provides a signal emitting member that can be used in connection with a variety of complex medical instruments, including an endoscope.

Accordingly, in one preferred and non-limiting embodiment, the present invention provides an endoscope storage cabinet for use with at least one endoscope having at least one signal emitting member associated therewith, the at least one signal emitting member configured to emit a signal indicative of at least one attribute of the at least one endoscope to which it is associated. The cabinet includes: an enclosed structure formed by a plurality of walls defining an inner area, wherein the inner area is accessible by at least one door; at least one hanger arrangement configured to support at least a portion of at least one endoscope positioned thereon; at least one signal receiving device associated with the enclosed structure and configured to receive the signal emitted by the at least one signal emitting member; and a local control device in communication with the at least one signal receiving device and configured to receive and process the signal emitted by the at least one signal emitting member.

In another preferred and non-limiting embodiment, the present invention provides an endoscope tracking system. This system includes: at least one computing device having a machine-readable storage medium containing instructions that, if executed, enable a processor to: (i) process at least one of the following: signals from at least one signal emitting member associated with at least one endoscope, data associated with the signals from the at least one signal emitting member associated with the at least one endoscope, or any combination thereof; and (ii) identify at least one attribute associated with the at least one endoscope.

In a further preferred and non-limiting embodiment, the present invention provides a signal emitting member. This signal emitting member includes: a flexible body configured for attachment to an item; a protruding portion extending from the body; and a signal emitting component attached to or embedded at least partially within the protruding portion and configured to emit a signal therefrom.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 13 is a front view of another embodiment of an endoscope storage cabinet according to the principles of the present invention, with certain portions removed for clarity;

FIG. 14 is a perspective view of a portion of an endoscope storage cabinet according to the principles of the present invention;

DETAILED DESCRIPTION OF THE PREFERRED EMBODIMENTS

Figure 1:
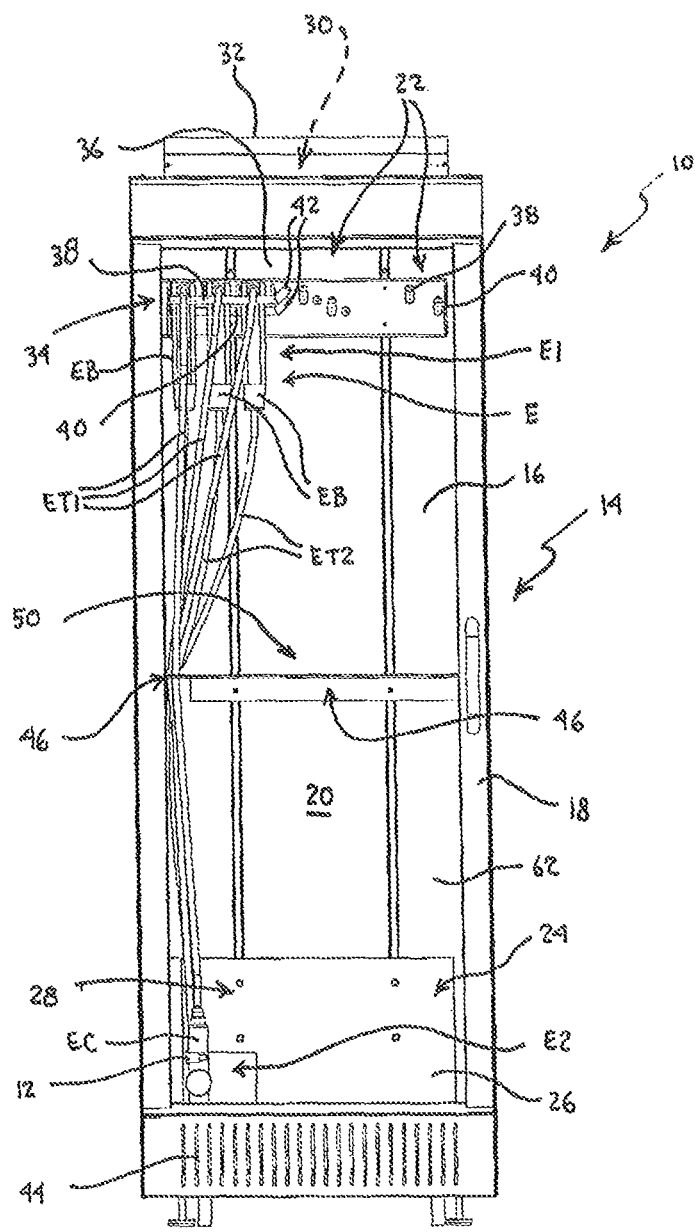
FIG. 1 is a front view of one embodiment of an endoscope storage cabinet according to the principles of the present invention.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

The present invention is directed to a storage cabinet, tracking system, and improved signal emitting member, all for use in connection with medical devices, e.g., an endoscope E. As is known, an endoscope E includes a first end E1 and a second end E2. The first end E1 of the endoscope E includes a main body EB, with an insertion tube ET1 and a connecting tube ET2 extending therefrom. The connecting tube ET2 connects and allows communication, e.g., electrical communication, between the main body EB (or its internal electrical components) and a light source connector EC, which is located at the second end E2 of the endoscope E The remaining electrical components and configuration of the endoscope E is well known in the art and the field of medical diagnostic systems.

In one preferred and non-limiting embodiment, and as illustrated in various views in FIGS. 1-10, an endoscope storage cabinet 10 is provided. This endoscope storage cabinet 10 is configured or adapted for use in connection with at least one endoscope E having at least one signal emitting member 12 attached to or associate therewith. This signal emitting member 12 is configured to emit a signal indicative of at least one attribute of the endoscope E to which it is attached or associated. Further, this signal emitting member 12 may be in the form of a tag, a transponder, a chip, or other signal emitting component capable of emitting a signal that carries data, preferably data associated with the item to which it is attached, i.e., the endoscope E. While, as discussed hereinafter, in a preferred and non-limiting embodiment, the signal emitting member 12 is a radio frequency emitting device, and it is envisioned that any emission/receiving structure, arrangement, and system can be utilized without departing from the spirit or scope of the present invention.

Figure 2:
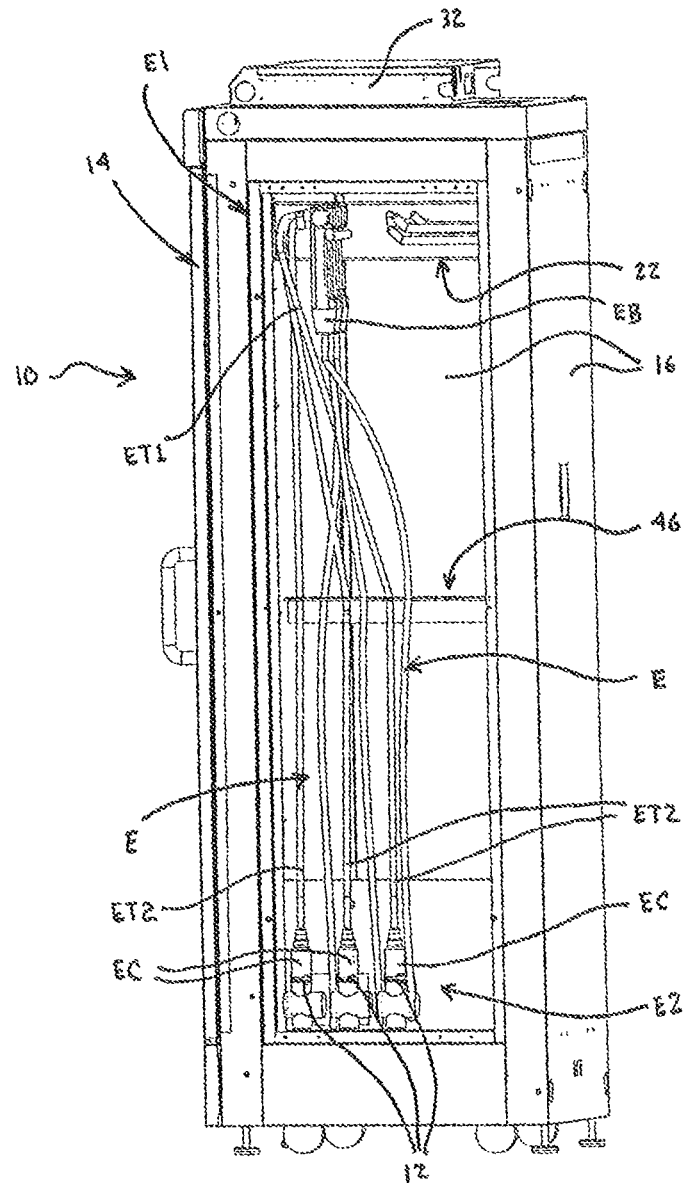
FIG. 2 is a perspective view of the endoscope storage cabinet of FIG. 1 with certain portions removed for clarity.

With reference to FIGS. 1-10, and in the illustrated embodiment, the storage cabinet 10 includes an enclosed structure 14 formed by walls 16 (upper, lower, and side) and a door 18. By using the door 18, one has access to an inner area 20 of the cabinet 10. Of course, in place of the door 18 any access structure can be used, such as a panel, a sliding panel, a drawer, or the like. In the inner area 20 and attached directly or indirectly to at least one of the walls 16 is at least one (and preferably multiple) hanger arrangements 22 for supporting at least a portion of an endoscope E positioned thereon. Preferably, and as best seen in FIGS. 1 and 2, the hanger arrangements 22 are designed to support the endoscope E at its first end E1 by making at least partial contact with the main body EB and the insertion tube ET1.

The storage cabinet 10 further includes at least one signal receiving device 24 that is attached to or associated with the enclosed structure 14 and utilized to receive the signal emitted from the signal emitting member 12 (attached to the endoscope E). In one preferred and non-limiting embodiment, the signal receiving device 24 is a planar antenna 26 structure that is positioned at or near a lower area 28 of the enclosed structure 14. In addition, and in this embodiment, two antennae 26 are provided, each of which is associated with one or more endoscopes E supported by respective hanger arrangements 22. In addition, a local control device 30 is attached to, associated with, or integrated within the storage cabinet 10, and this local control device 30 is in communication with the signal receiving devices 24 and used to receive and process the signals emitted by the signal emitting members 12.

In one preferred and non-limiting embodiment, the local control device 30 comprises a variety of electrical components, circuit boards, storage medium, computing devices, and the like for receiving and processing signals and other data streams. Therefore, this local control device 30 may take a variety of forms, but normally includes a processor or other computing means, as well as a temporary or permanent storage medium, for executing program instructions and otherwise implementing the embedded, loaded, or received software code. In addition, this local control device 30 may be used to interface with and/or control other electrical components and sub-systems within the cabinet 10.

Figure 6:
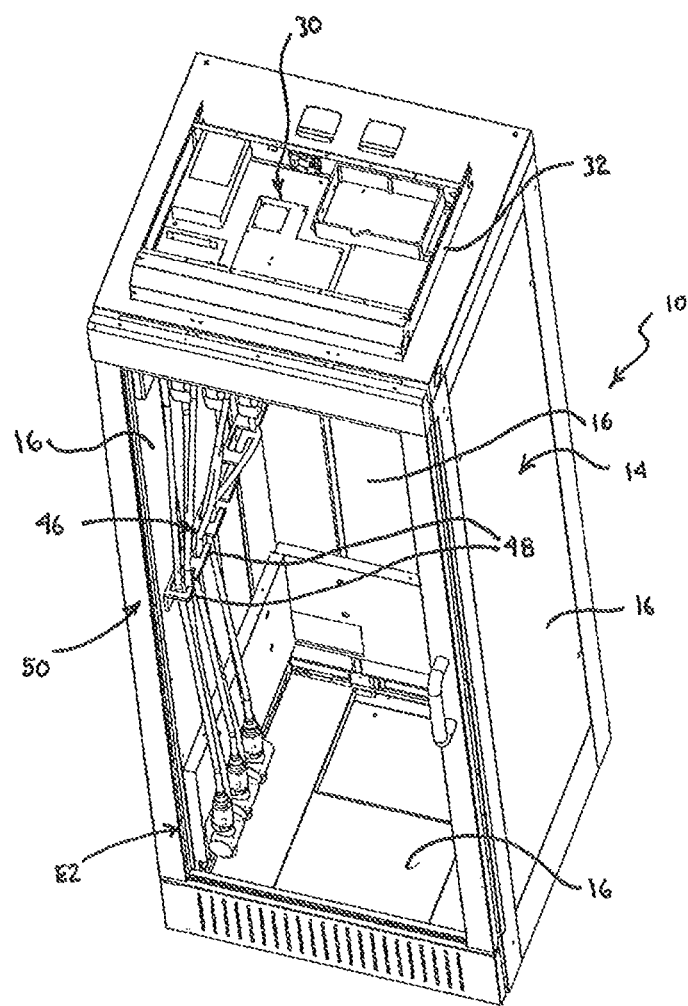
FIG. 6 is a perspective view of the endoscope storage cabinet of FIG. 1 with certain portions removed for clarity.
Figure 7:
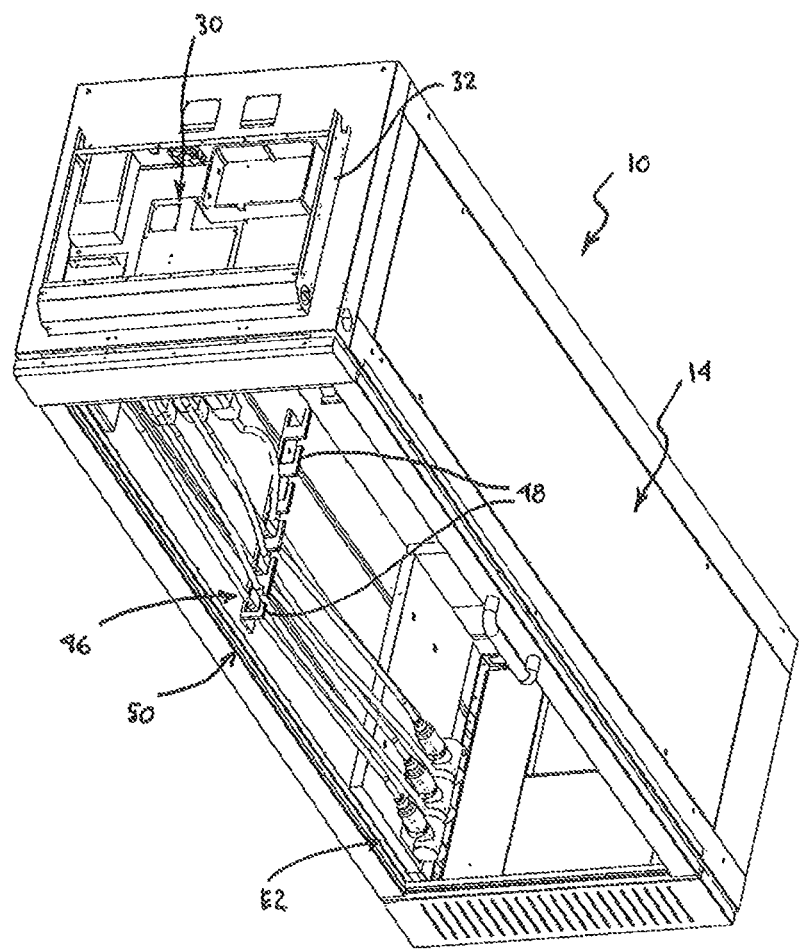
FIG. 7 is a further perspective view of the endoscope storage cabinet of FIG. 6.

As seen in FIGS. 6 and 7, and with continued reference to FIG. 1, the local control device 30 (including all of its underlying components) may be contained in a housing 32 positioned on the top of the enclosed structure 14. By positioning the local control device 30 and its components on top of the enclosed structure 14, these electrical systems and devices are kept safe and distant from potential contact, interference, vandalism, etc.

In order to provide another layer of security to the cabinet 10, the door 18 may be locked by at least one locking arrangement that is in direct or indirect communication with the local control device 30. For example, the cabinet 10 may be locked with an electrically-operated lock, actuated through application software embedded or loaded on the local control device 30, thereby providing physical security and preventing access to the inner area 20 of the cabinet 10. This locking arrangement can be "defeated" with a key-operated, manual override, if necessary. Otherwise, and as discussed hereinafter, some interface device can be provided to allow restricted user access based upon user identification, authority levels, authentication systems, and the like. Further, it is envisioned that the locking arrangement can be controlled remotely by or through a central control device or remote computer.

Figure 3:
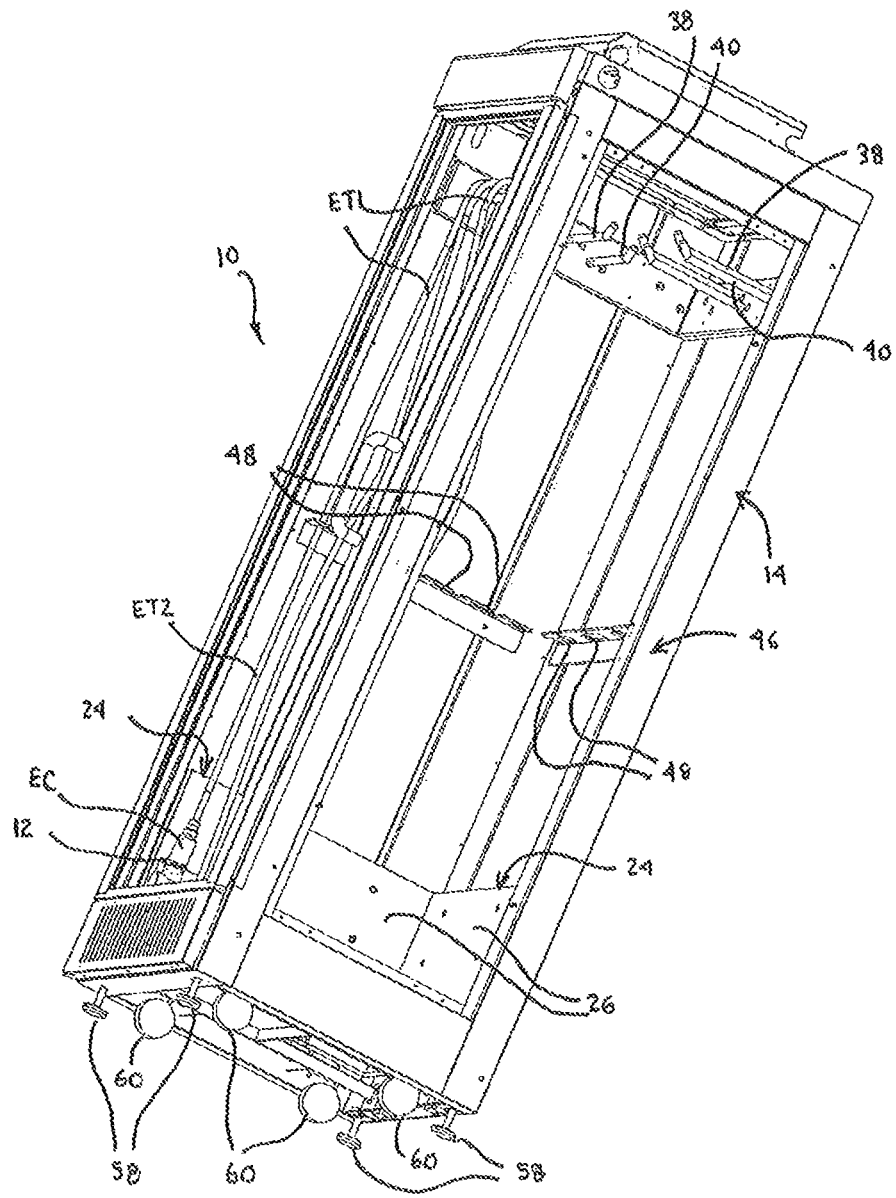
FIG. 3 is a further perspective view of the endoscope storage cabinet of FIG. 2.
Figure 4:
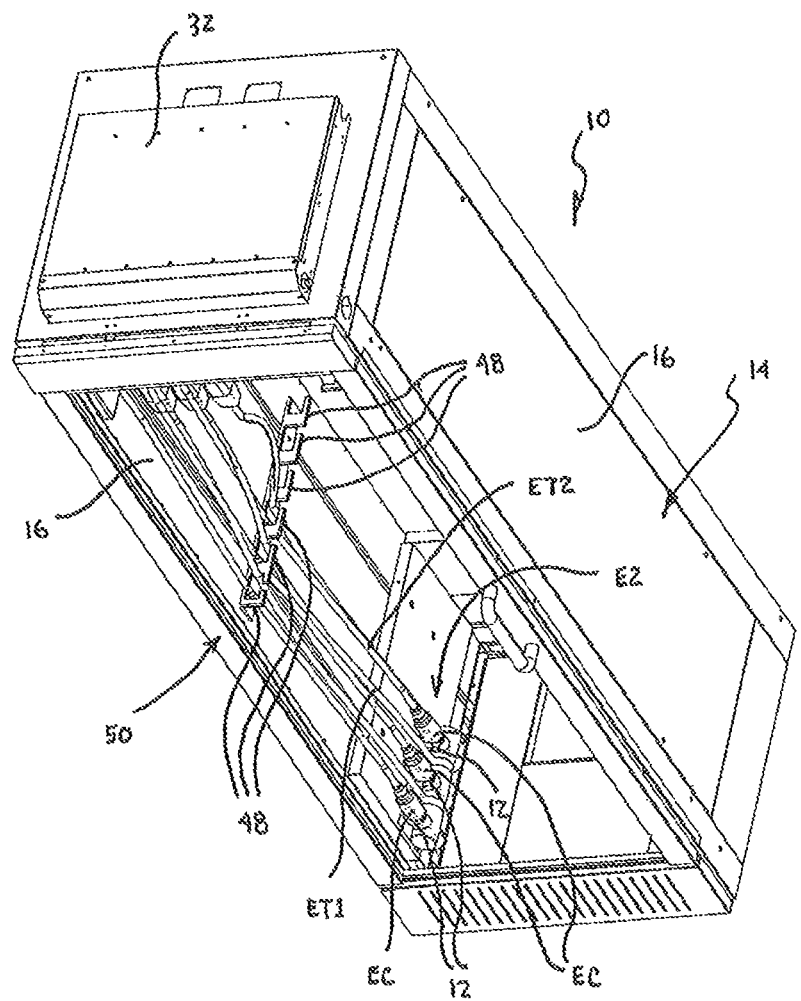
FIG. 4 is a perspective view of the endoscope storage cabinet of FIG. 1.
Figure 5:
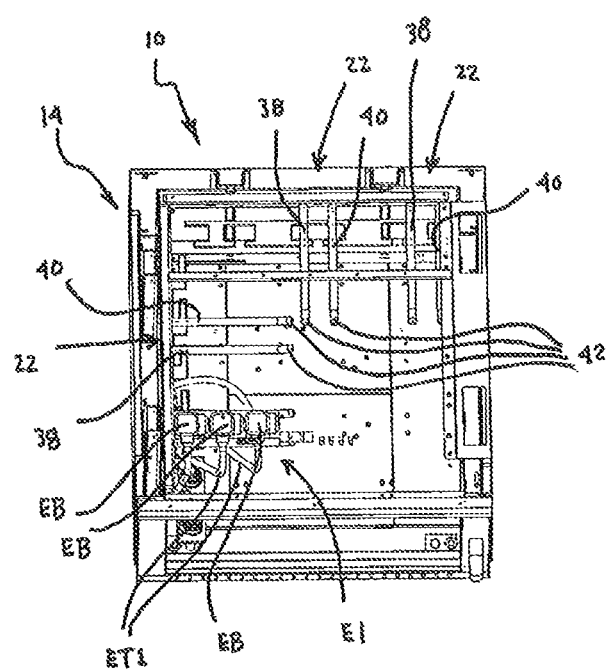
FIG. 5 is a top view of the endoscope storage cabinet of FIG. 1 with certain portions removed for clarity.

As best seen in FIGS. 1-3, and in another preferred and non-limiting embodiment, the hanger arrangement 22 is in the form of projecting members 34, which extend from an inner surface 36 of a wall 16 of the enclosed structure 14. These projecting members 34 may also be attached to the wall 16 indirectly by first attaching a bracket to the wall 16, and the projecting members 34 to the bracket. Further, in this embodiment, multiple hanger arrangements 22 are included, and each of these hanger arrangements 22 include a set of projecting members 34, i.e., a first projecting member 38 that is spaced from and offset with respect to a second projecting member 40. By using this unique offset design, the first projecting member 38 is configured for contact with the insertion tube ET1, and the second projecting member 40 is configured to contact at least a portion of the endoscope main body EB. Still further, by using this unique offset design, the endoscopes E are held securely, as well as in a vertical orientation, which, as discussed hereinafter, lends itself to better communication between the signal emitting members 12 and the signal receiving devices 24.

In this embodiment, each set of projecting members 34 is sized and shaped so as to effectively retain multiple endoscopes E, such as three endoscopes E, as best illustrated in FIGS. 1 and 2. In addition, and in order to further secure the endoscopes E to the projecting members 34, each projecting member 34 may include a beveled end 42. This will minimize the risk of accidental movement or dislodgment of the endoscope E from the hanger arrangements 22. Of course, it is further envisioned that some local locking device or arrangement can be used in connection with each hanger arrangement 22 to provide additional security. For example, each of these local locking arrangements could be electrically operated by or through the local control device 30, thereby only selectively allowing certain endoscopes E within the cabinet 10 to be inserted or removed.

In another embodiment, the cabinet 10 is ventilated, such as through exhaust fans positioned at or near the top of the enclosed structure 14, and a filtered air inlet vent 44 can be positioned at or near the lower area 28 of the cabinet 10, on the door 18, or on some other wall 16 of the enclosed structure 14. The resulting air flow aids in the drying process of any wet or damp endoscopes E positioned in the inner area 20. However, the cabinet 10 may be a positive pressure ventilation system by pulling filtered air into the inner area 20 of the cabinet 10 and allowing it to escape through openings, such as the vent 44 (which would become an outlet vent).

With reference to FIGS. 4 and 6-9, and in another preferred and non-limiting embodiment, a hook arrangement 46 is provided. This hook arrangement 46 is configured or designed to contact and retain at least a portion of the endoscope E supported by the hanger arrangement 22. In particular, this hook arrangement 46 may be configured to retain or hold a portion of the insertion tube ET1 and the connection tube ET2. In this embodiment, the hook arrangement 46 includes multiple spaced hooks 48, each configured to contact and retain at least a portion of a specified endoscope E supported by a specifically-positioned hanger arrangement 22.

Figure 8:
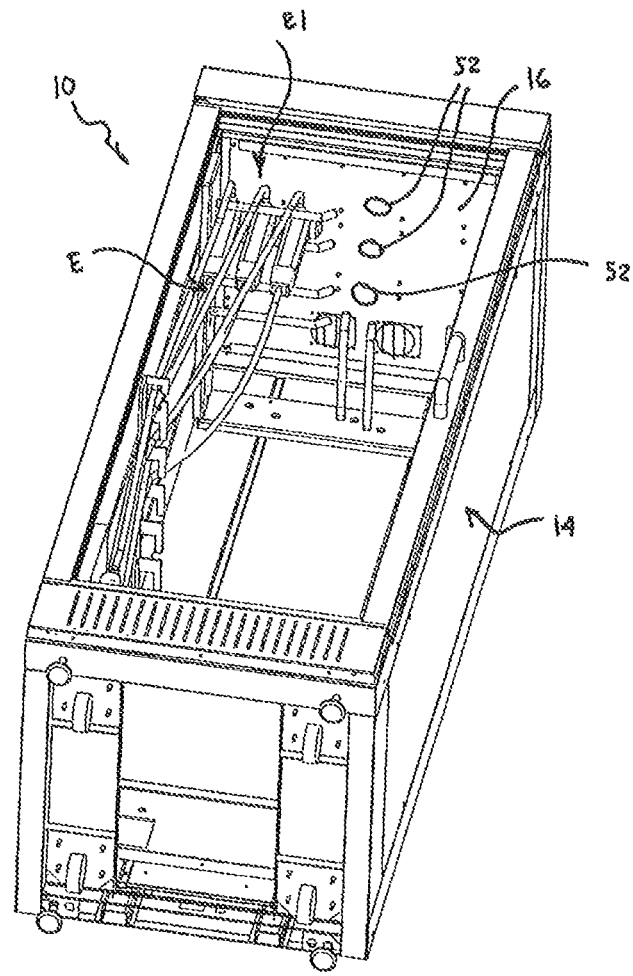
FIG. 8 is another perspective view of the endoscope storage cabinet of FIG. 1 with certain portions removed for clarity.
Figure 9:
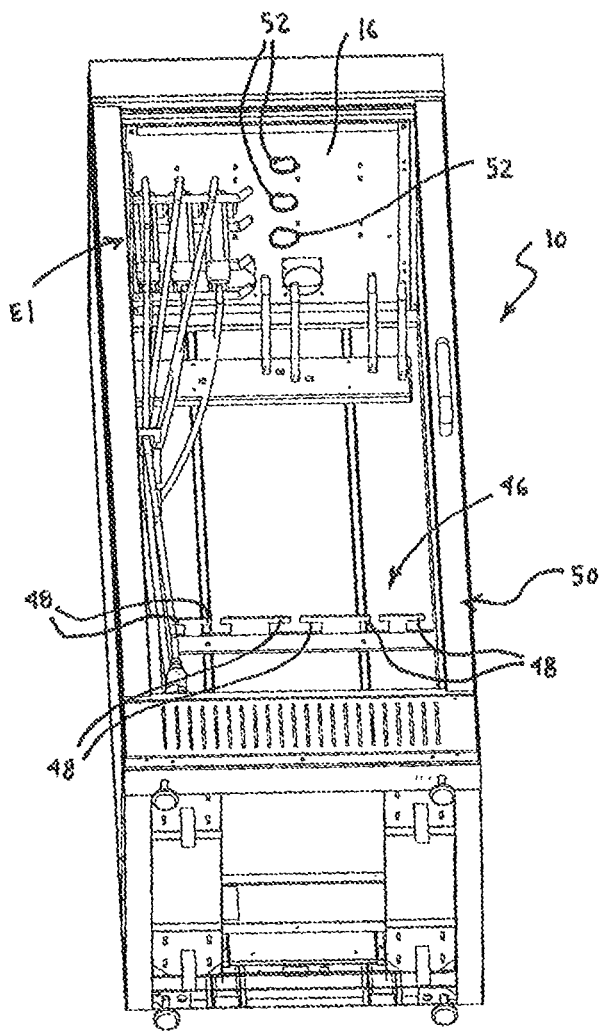
FIG. 9 is a further perspective view of the endoscope storage cabinet of FIG. 1 with certain portions removed for clarity.

With reference to the preferred and non-limiting embodiment illustrated in FIGS. 7-9, each hanger arrangement 22 is sized and configured to hold three endoscopes E, such that three hooks 48 are provided for each hanger arrangement 22. These hooks 48 are spaced and configured to contact and hold a portion of a respective endoscope E. Accordingly, in the embodiment of FIGS. 1-10, where four hanger arrangements 22 are utilized, each hanger arrangement includes a respective three specifically-positioned hooks 48 for contacting a portion of a respective endoscope E. In this manner, and in this embodiment, the storage cabinet 10 is configured to hold 12 endoscopes E.

With further reference to FIGS. 7-9, the hook arrangements 46 are positioned at a middle area 50 in the enclosed structure 14, such as at the midline of the cabinet 10. In addition, and based upon the asymmetric or spaced arrangement of the hooks 48, each endoscope is safely positioned and held near the inner surface 36 of the wall 16 in the cabinet 10 (which prevents or minimized potential damage to the endoscope E). In addition, such positioning and placement orients the second end E2 of the endoscope E near the signal receiving device 24, which permits better reception of the signals emitted from the signal emitting member 12. Still further, the combined use of the unique hanger arrangements 22 and hook arrangement 46 allows for the configuration of the pitch of the endoscope E with respect to the signal receiving devices 24. Thus, this arrangement eliminates or minimizes variability in the system, which enhances the overall performance and accuracy thereof.

As discussed above, the signal receiving devices 24, e.g., the antennae 26, may be positioned in a lower area 28 of the cabinet 10. In this embodiment, these antennae 26 are designed for communication with the signal emitting members 12, which may be in the form of radio frequency identification (RFID) tags. In one embodiment, these tags are HF ISO tags, but may be UHF, EPC, or any other type of RFID tag. Again, the location and positioning of the antennae 26 is such that a light source connector EC at the second end E2 of the endoscope E aligns with a respective antenna 26. Since the length of this connector EC is relatively similar across manufacturers, accurate antenna 26 placement can be calibrated depending upon this distance.

In another embodiment, and as illustrated in FIGS. 8 and 9, one or more light members 52 can be provided, such as in the form of overhead lighting in the inner area 20 of the cabinet 10. In this embodiment, these light members 52 are managed through the software or other program instructions on the local control device 30, or other electrical component in the storage cabinet 10. For example, these light members 52 may be colored lights, e.g., red lights that are turned on to indicate a problem within the cabinet 10, or otherwise indicate some issue within the cabinet 10 or with the endoscopes E positioned in the cabinet 10. Still further, and as discussed, the electrical components can be situated above the enclosed structure 14 in a housing 32, which provides radio frequency shielding, and further allows for the maximization of the space in the inner area 20 of the enclosed structure 14 for the storage of endoscopes E.

Figure 10:
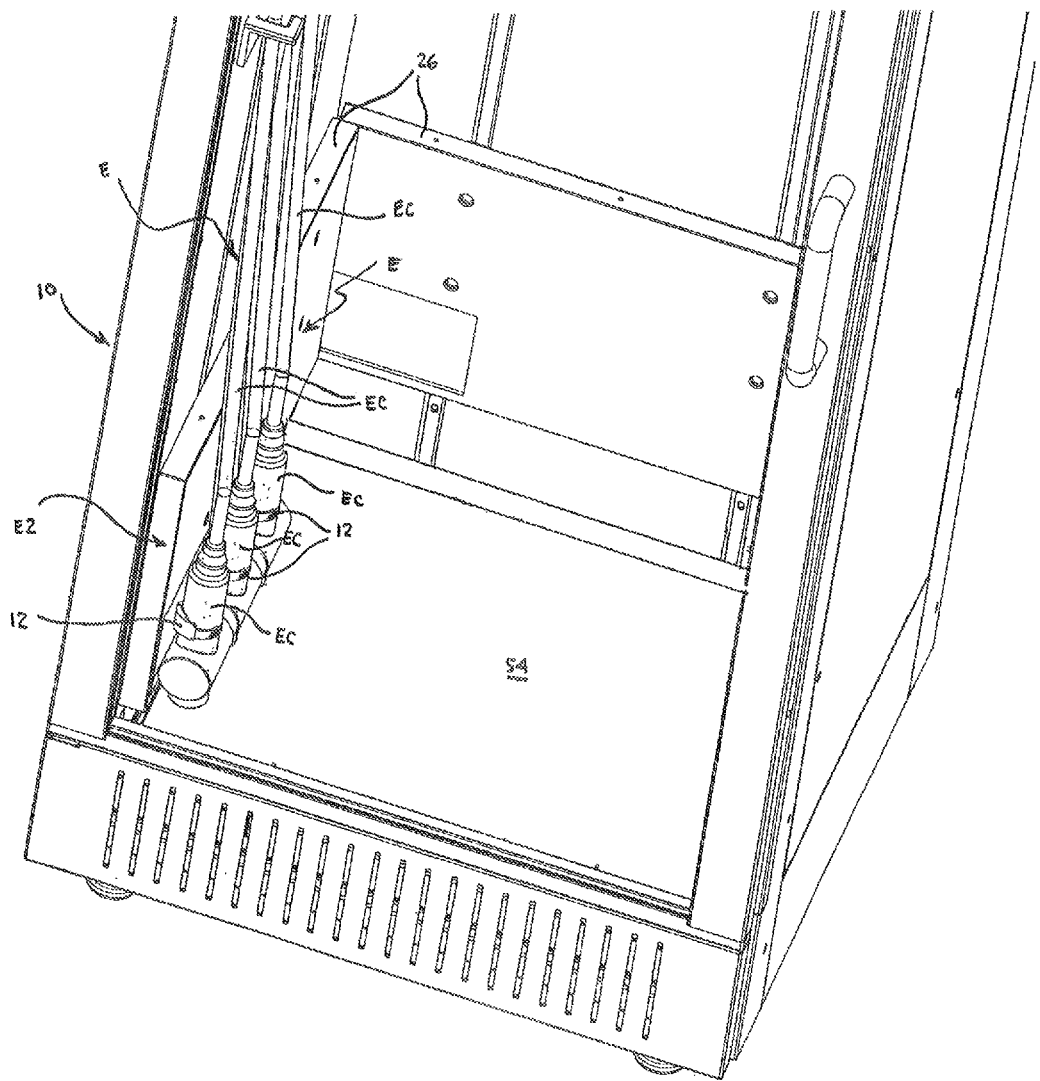
FIG. 10 is a perspective view of a portion of the endoscope storage cabinet of FIG. 1.

Still further, and as illustrated in FIG. 10, a drip pan 54 can be positioned as the floor of the enclosed structure 14, and this drip pan 54 is sized and shaped so as to capture any liquid dripping from the second end E2 of the endoscope E. As illustrated in FIGS. 1-3, the storage cabinet 10 may include legs 58 for supporting the enclosed structure 14 and raising the enclosed structure 14 from ground level. These lets 58 may be adjusted or adjustable, such as when used in connection with wheels 60. Such wheels 60 (or casters) allow for the effective mobilization and movement of the cabinet 10 from location to location within the hospital or office.

Figure 11:
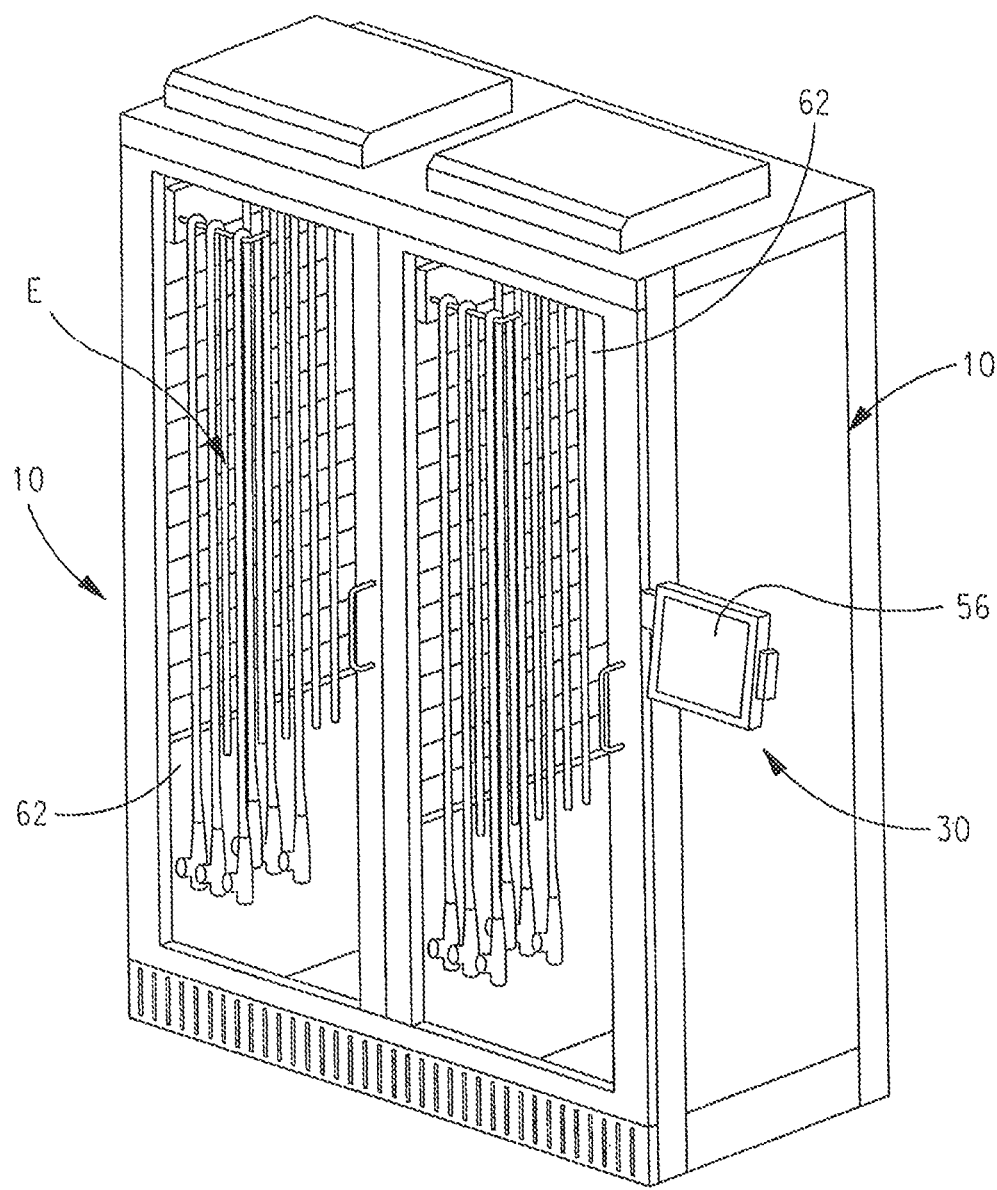
FIG. 11 is a perspective view of another embodiment of an endoscope storage cabinet according to the principles of the present invention.
Figure 12:
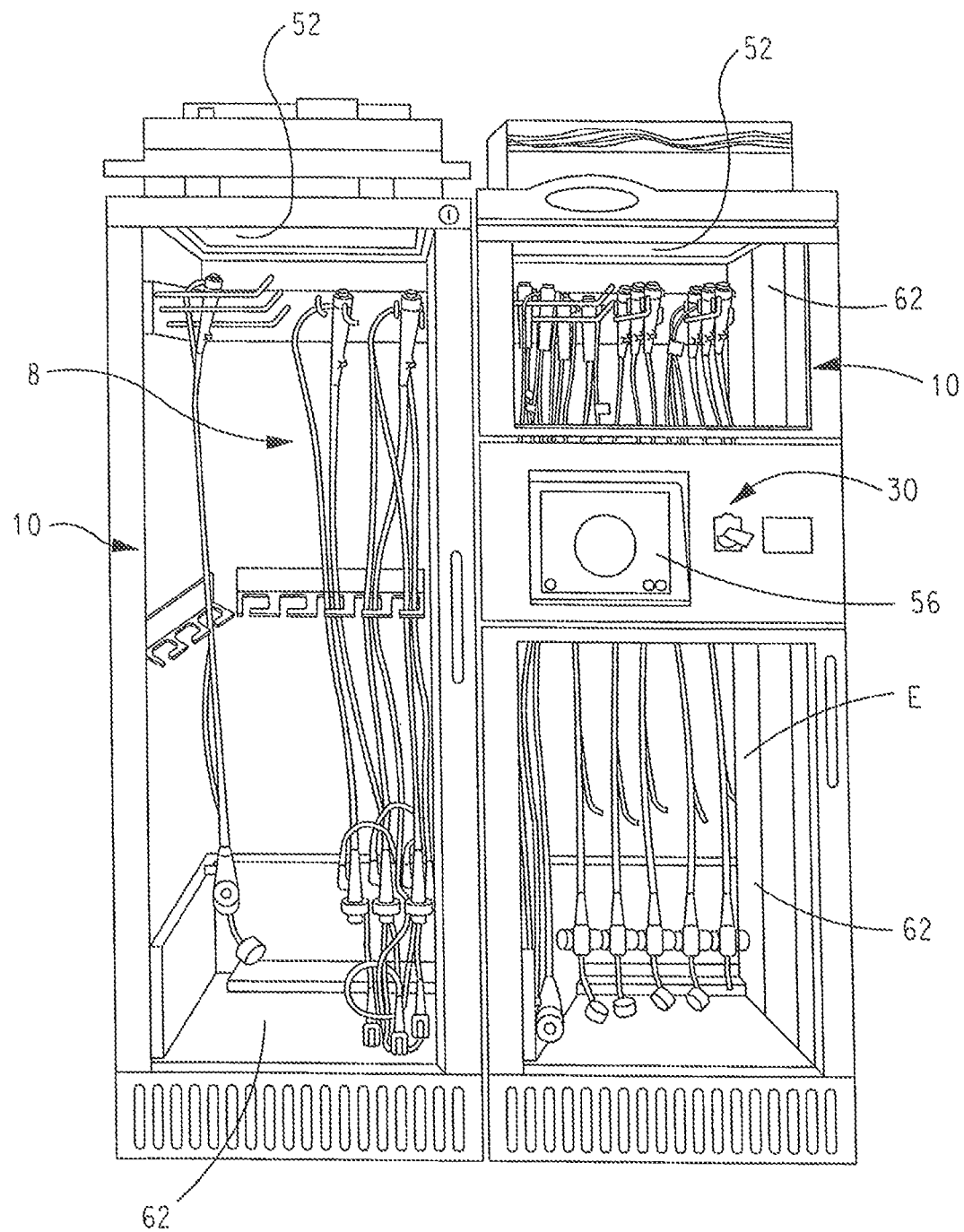
FIG. 12 is a perspective view of further embodiment of an endoscope storage cabinet according to the principles of the present invention.

In another preferred and non-limiting embodiment, and as illustrated in FIG. 11, two cabinets 10 may be positioned side by side and can be controlled by the same local control device 30. Further, in this embodiment, a visual display device 56 is attached to the side of the cabinet 10, and this visual display device 56 may be in communication (or be integrated) with the local control device 30, some computing device associated with or integrated with the cabinets 10, or through remote communication to some other central control device (as discussed in detail hereinafter). In another preferred and non-limiting embodiment, and as illustrated in FIG. 12, this visual display device 56 may also be incorporated on the front of one or both of the cabinets 10, and serves to provide an interface between the user and the overall control system.

As also illustrated in FIG. 1, the door 18 may at least partially be formed from glass 62 for allowing a person to view its contents without requiring access. Of course, if such visibility is not desired, the door 18 can be made from any suitable opaque material or structure. Still further, any of the portions of the walls 16 of the enclosed structure 14, including the top, floor, side, etc., may be shielded to prevent signals emitted in the inner area 20 from escaping the cabinet 10 (possibly causing interference with other devices and components).

In another preferred and non-limiting embodiment, and as illustrated in FIG. 13, the hanger arrangement 22 may be in the form of a wire frame 64. In this embodiment, the wire frame 64 includes a first portion 66 and a second portion 68, where the first portion 66 is similar to the first projecting member 38, and the second portion 68 is similar to the second projecting member 40. Accordingly, the above-discussed offset design is provided.

As also illustrated in the embodiment of FIG. 13, the wire frame 64 can be attached to the inner surface 36 of the wall 16 through the positioning of a bracket 70. This bracket 70 may include sleeves 72 configured to removably accept a portion of the wire frame 64. This will also lead to the ability to specifically configure the wire frames 64 within the inner area 60 of the cabinet to provide the most effective positioning and spacing of the endoscopes E.

As also discussed above, the use of the unique hook arrangement 46 provides effective and appropriate spacing between the endoscopes E, such as between the insertion tube ET1 and connection tube ET2 of each endoscope E. One version of such a hook arrangement 46 is illustrated in FIG. 14, again demonstrating the spacing and setting of the pitch of the multiple endoscopes E in the cabinet 10.

In any of the above-discussed embodiments, the cabinet 10 may be accessed through the use of a PIN-number, a user account/password combination, validation of a user through the use of a radio frequency embedded identification card (typically HID or barcode), etc. Additionally, biometric identification, such as finger and/or thumb print, eye-iris and retina scanning, and similar authentication and authorization techniques and methodologies can be used. Further, the cabinet 10 may be equipped with a barcode reader for use in obtaining data, such as patient EMR or account numbers, which represent unique identification of the patient and/or the visit. Some or all of these data receiving and processing devices and components can interface with the local control device 30, as well as some other remote or centrally located control device. Still further, a local control device 30, or any of these other electrical components and data gathering devices, may be integrated with or otherwise interfaced with the hospital computer systems and network.

In operation, endoscopes E may only be removed after an authorized user accesses the cabinet 10, and selects the patient from a list that includes all potential endoscopy patients. An ADT (admission discharge transfer) interface feed may be utilized. The system includes interfaces, which receive the patient name, doctor, procedure, and various types of related data. This data is updated automatically so that the user is always presented with real-time data. Further, this link between a patient and an endoscope E may be maintained in perpetuity, such that patients can be alerted due to some issue with an endoscope E. This may occur when a damaged endoscope E is not cleaned properly and exposed patients must be contacted to make appropriate arrangements and to take needed precautions. In this manner, only a limited number of patients need to be contacted.

Accordingly, and as discussed in the various embodiments of the storage cabinet 10 discussed above, many unique and beneficial features can be provided. For example, by positioning the electronics and other electrical components on top of the cabinet 10, the inner area 20 is less cluttered and allows for the long endoscopes E to hang freely within. In addition, the housing 32, which may be a hinged cover, obscures certain functions from the casual observer. The server or other local control device 30 can be positioned also on top of the cabinet 10 to allow for easy implementation, including retrofitting, and permits easy maintenance.

By placing the signal emitting members 12 on the light source connector EC of the second end E2 of the endoscope E, the distance from the top of the hanger arrangement 22 is fixed and based upon the particular manufacturer. The signal emitting members 12 are then in close proximity to the antennae 26, and the pitch that is set by the hook arrangement 46 eliminates or reduces the chance of interference between the signal emitting members 12. The local control device 30 (or remotely-situated central computing device or controller) allows the user to manage the system in process, such as through the visual display device 56. Again, this visual display device 56 may be a touch screen for use in interacting with the cabinet 10, and may swing with the door 18 to provide full access to the inner area 20, as well as convenient access to the visual display device 56. As discussed, certain additional data receiving devices, such as in a RFID reader or a barcode reader, may be integrated with the cabinet 10 to permit only authorized access and/or beneficial functionality, e.g., patient selection. As discussed hereinafter, certain standard "buttons" may be provided for anyone to appropriately locate a particular endoscope E or obtain an inventory of the cabinet 10, even if the user is not logged into the tracking system.

The filtered vents 44 provide for clean air circulation within the cabinet 10. As discussed above, the endoscopes E are held securely, i.e., in a vertical manner, in the cabinet 10, and this reduces the chances of damaging the expensive endoscopes E. The cabinet 10 may be manufactured from a secure and easy-to-clean material, and the projecting members 34 and/or hooks 48 can be manufactured from a non-abrading plastic. The asymmetric layout and positioning between the hanger arrangements 22 and the hooks 48 permit the endoscopes E to be "pulled" into the hooks 48 by gravity. Further, since the pitch is fixed, the endoscope E is prevented from swinging within the cabinet 10.

Figure 15A:
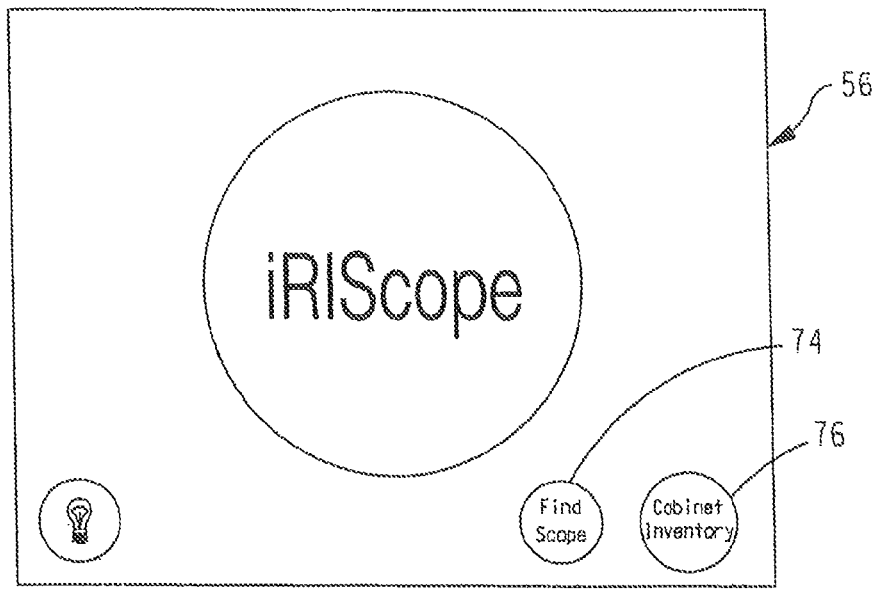
FIG. 15A is one screenshot in an endoscope tracking system according to the principles of the present invention.
Figure 15B:
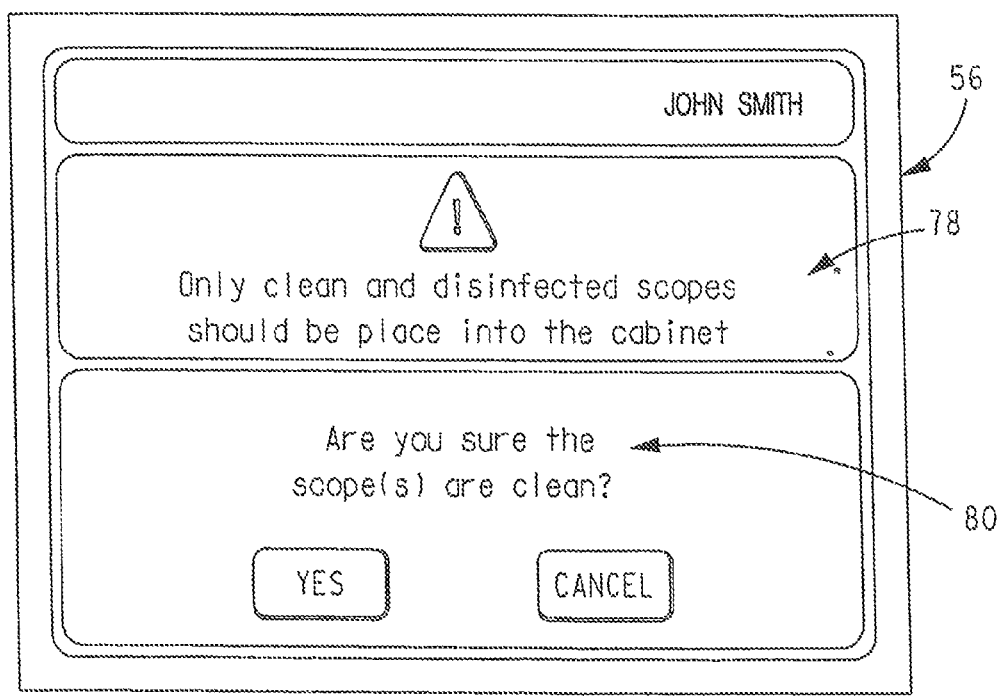
FIG. 15B is another screenshot in an endoscope tracking system according to the principles of the present invention.

With reference to FIG. 15, and as discussed above, the visual display device 56 can provide certain information to the user. The above-discussed "buttons" can be located on the visual display device 56, such as a "find scope" button 74 and a "cabinet inventory" button 76. In addition, a challenge screen 78 can be provided to ensure that only clean and disinfected endoscopes E are placed in the cabinet 10. For example, this challenge screen 78 may include a query 80 asking the user if he or she is sure that the endoscope E is clean (prior to positioning within the cabinet 10). This is important to ensure that a "dirty" endoscope E does not contaminate other "clean" endoscopes E in the cabinet 10.

In a still further preferred and non-limiting embodiment, a reprocessing station 82 is provided. This reprocessing station 82 may include a touch-screen computer, e.g., a local control device 30 and visual display device 56, an RFID reader, and an access control system, e.g., an HID or biometric reader. All of these units and components may be mounted on a swing-arm for ease of use. When using a cabinet 10 as a reprocessing station 82, some or all of the physical or electrical components discussed above can be used. However, the reprocessing station 82 preferably includes the components necessary for a user to apply any signal emitting members 12 to the endoscopes E, scan these signal emitting members 12 and create the appropriate correlation between them for use in connection with an endoscope tracking system 84, as illustrated in one preferred and non-limiting embodiment in FIG. 16.

Further, the user can scan the signal emitting members 12 in order to track workflow and generate other data. Still further, the endoscope tracking system 84 may be in communication with one or more disinfection machines 86, which may be in communication with or otherwise positioned near the reprocessing station 82. Such disinfection machines 86 use certain chemical solutions to achieve high-level disinfection and/or sterilization of the endoscopes E. Accordingly, the endoscope tracking system 84 can be used in connection with the disinfection machine 86 in order to capture data related to the adherence to specified cleaning protocols, as well as track and/or analyze the actual chemical solutions used in a particular washer or disinfection machine 86. Such information and data allows for the calculation of permissible concentration levels, expiration dates of chemicals, authorized technician validation, etc.

Figure 16:
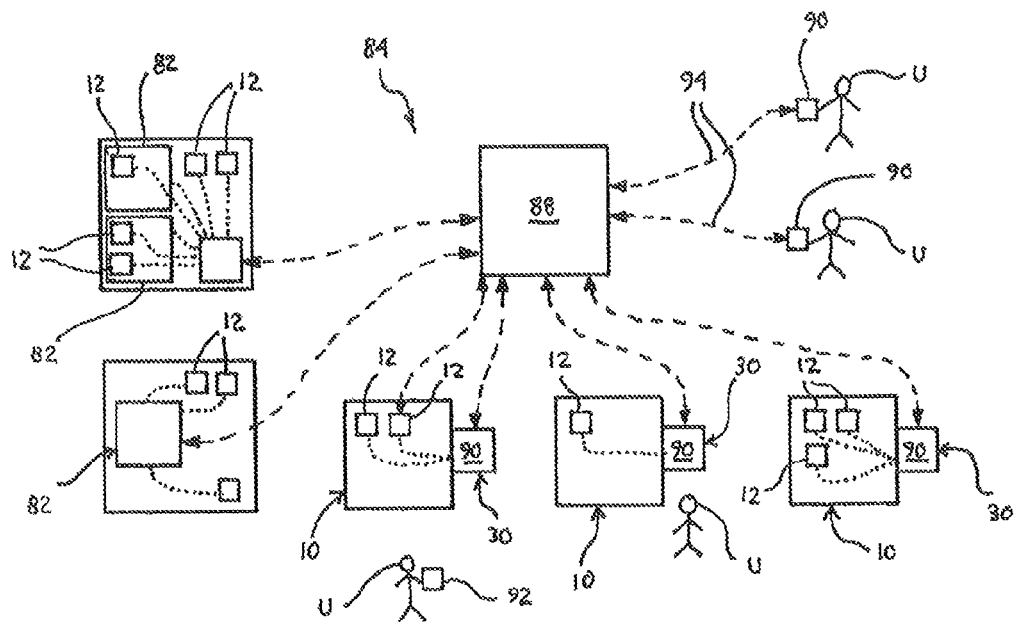
FIG. 16 is a schematic diagram of an endoscope tracking system according to the principles of the present invention.

Accordingly, and in the embodiment of FIG. 16, the endoscope tracking system 84 includes the appropriate computing devices and components in order to process signals emitted from a signal emitting member 12, data associated with these signals, etc., and this information is used to identify one or more attributes associated with a particular endoscope E. This data may also be transmitted by a local control device 30 of any number of cabinets 10. Of course, as discussed above, other components and portions of the overall process, e.g., the disinfection machines 86, the reprocessing station 82, etc., may also produce data that is tracked or otherwise captured and processed within the endoscope tracking system 84. Accordingly, the attribute that is tracked and processed may be endoscope data, disinfection stage data, disinfection device data, damage data, cleaning data, use data, associated user data, location data, alert data, time data, or the like.

In one preferred and non-limiting embodiment, the endoscope tracking system 84 includes a central control device 88 that is in direct or indirect communication with the storage cabinets 10, the reprocessing station 82, the disinfection machines 86, directly with the signal emitting member 12, the signal receiving device 24, or any other component within the overall system and arrangement. Accordingly, it may be this central control device 88 that is supportive of or enables the generation of the initial correlation between a specific signal emitting member 12 and a specific endoscope E.

Further, and within the context of this preferred and non-limiting embodiment of the endoscope tracking system 84, the local control device 30 is in the form of a local computing device 90 that positioned on or near the cabinet 10, which is configured to communicate and control one or more of the components of the cabinet 10. In addition, the central control device 88 may be in the form of a remote central control device 88 that is in communication with the local computing device 90 of each of the cabinets 10. Of course, this central control device 88 may be local to one or more of the cabinets 10, and may constitute the primary controller to engage in the communication with and processing of signals derived from the signal emitting members 12 or other portions of the overall process and arrangement.

Various communication links of one preferred and non-limiting embodiment of the system 84 are illustrated in FIG.

16, which demonstrates the use of the central control device 88 in communication with other devices and components within the overall system 84. For example, this central control device 88 may be in communication with a local computing device 90 that communicates with the reprocessing station 82 and/or the disinfection machine 86, a local computing device 90 that serves as a local control device 30 in a specified cabinet 10, a local computing device 90 that is attached to or otherwise associated with the cabinet 10, or even directly to the signal emitting members 12 or signal receiving devices 24 within a specified cabinet 10. Accordingly, any number of communication links and variations can be implemented within the endoscope tracking system 84 of the present invention for use in data gathering and processing.

As also seen in FIG. 16, and as discussed above, each individual user U may also hold an authorization/authentication card 92 that can be used to interact with one or more of the components of the storage cabinet 10, the reprocessing station 82, the disinfection machine 86, etc. This card 92 may be in the form of an RFID card that serves to uniquely identify the user U. Of course, and as discussed, various techniques and methods can be used to authenticate, authorize, and/or associate a particular user U with a cabinet 10, a reprocessing station 82, a disinfection machine 86, a signal emitting member 12, an endoscope E, etc.

Figure 17:
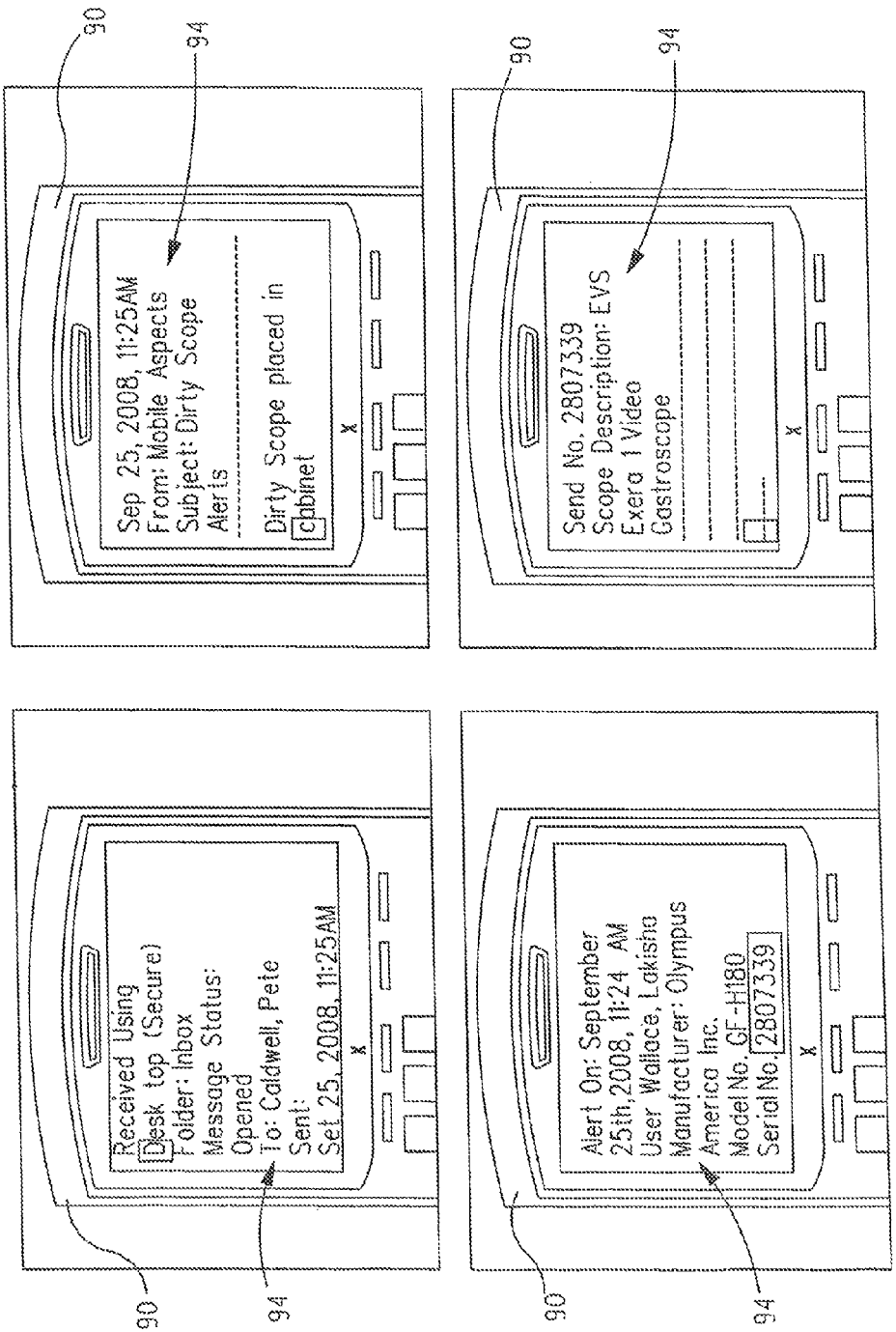
FIG. 17 is multiple screenshots of specific alert messages that can provide to a user in an endoscope tracking system according to the principles of the present invention.

As also illustrated in schematic form in FIG. 16, and with reference to the exemplary screen shots in FIG. 17, the endoscope tracking system 84 may also generate alert data 94 based upon the determined attribute of the endoscope E. For example, this alert data 94 can be derived or generated by the central control device 88 and subsequently communicated to the local control device 30 of the cabinet 10 (for use in providing visual alerts, e.g., blinking light members 52), or transmitted to the local computing device 90 of a specified user U. For example, text alerts can be sent to the computing device of an administrative user U, such as to his or her PDA, cellular phone, or similar device, or via e-mail. Based upon the accuracy provided by such a tracking system 84, specific and detailed notices, textual messages, and other alerts can be exchanged to provide accurate determination of issues associated with a particular cabinet 10, a particular endoscope E, a particular user U, or the like. All of this information and data can be used to ensure safety and security, track "dirty" endoscopes E, track missing endoscopes E, provide user association data, etc.

In one preferred embodiment, damaged endoscopes E are checked "out-for-repair" using the reprocessing station 82. This functionality tracks all of the associated relationships for the endoscope E. Accordingly, if a specific technician is repeatedly associated with a damaged endoscope E, this correlation is quickly identified. Also, if a specific doctor is declaring endoscopes E to be damaged more often than is typical, or if the endoscopes E are returned from repair with "no-problem-found," there is now a clear fact-based record for management to use to correct the problem.

In addition, and in one preferred and non-limiting embodiment, both the reprocessing station 82 and the individual storage cabinets 10 share the capability to "find scopes" using button 74. This feature identifies the location and use of individual endoscopes E in the pool. They may be identified as "in-use" (and associated with a patient, procedure, and/or doctor) or "in the disinfection process" (within a specified disinfection machine 86, a washer, just removed from a washer, etc.), "out-for-repair" (and the location of the repair facility, stage of repair, expected completion, etc.), or "present" in one of the cabinets 10. If the endoscope E is in a specified cabinet 10, the system identifies which cabinet 10, and in which location, e.g., within the entire hospital campus, within a different building, in a specified department, etc. All of this information can be maintained on local or remote databases that are associated with or otherwise in communication with the central control device 88, any of the local computing devices 90, or any of the local control devices 30. Accordingly, a server may maintain records of all transactions within the system 84, and may also manage the interfaces with other systems for data feeds, such as patient and/or procedure information.

As discussed above, alert data 94 provides a greater understanding of conditions throughout the system 84. Accordingly, the system 84 is programmed to verify and control the placement of only disinfected endoscopes E in specified cabinets 10. Accordingly, if an endoscope E not identified as "clean" (by virtue of tracking at the reprocessing station 82) is placed into a cabinet 10, the system can remotely lock the affected cabinet 10, flash the light members 52 in that cabinet 10, or provide some other oral, tactile, visual, or similar indication. In addition, a textual alert may be sent to the supervisors or administrative users U, specifically those supervisors that have the authorization to clear such locked-cabinet situations. However, and as discussed above, in order to provide certain further precautions, the challenge screen 78 can be used, which provides the query 80. This allows the local user U to validate that the endoscope E is, indeed, clean before causing a lockdown of the cabinet 10.

Still further, if an endoscope E is not placed back within the cabinet 10 or otherwise scanned within the system 84 for a specified period of time, it may be deemed as being a risk for loss and/or theft. Accordingly, such alert data 94 is collected and processed in real-time and arrives, for example, within one minute, to allow the supervisor to address the issue in a timely fashion. This alert data 94 may include information regarding who last handled the endoscope E, the last known status and/or use of the endoscope E, specific identifying information associated with the endoscope E (e.g., make, model, serial number, etc.), etc. Again, reference is made to the exemplary screen shots illustrated in FIG. 17, which can be displayed on the administrator's PDA, cellular phone, computer, etc.

In a still further embodiment of the present invention, an improved signal emitting member 12 is provided. As shown in one preferred and non-limiting embodiment in FIG. 18, the signal emitting member 12 includes a flexible body 96 that allows attachment to an item, such as an endoscope E. The signal emitting member 12 further includes a protruding portion 98 that extends from the body 96, and a signal emitting component 100 attached to or embedded at least partially within the protruding portion 98. It is this signal emitting component 100 that, whether passively or actively, generates and emits the signal that includes data associated with the item to which it is attached. The use of this flexible body 96 allows the signal emitting member 12 to be stretched and attached to various portions of certain items, such as medical devices, and in one preferred and non-limiting embodiment, the light source connector EC of an endoscope E.

Figures 18, 19, 20:
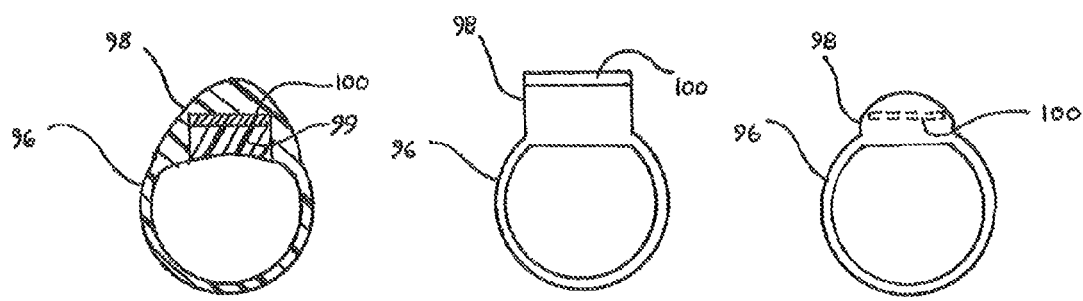
FIG. 18 is a side, sectional view of one embodiment of a signal emitting member according to the principles of the present invention.
FIG. 19 is a side view of another embodiment of a signal emitting member according to the principles of the present invention.
FIG. 20 is a side view of a further embodiment of a signal emitting member according to the principles of the present invention.

This flexible body 96 can be formed from a variety of materials. For example, any part or internal portion of the flexible body 96 can be formed at least partially from rubber, silicone, a molded material, a radio frequency absorbent material, a chemical resistant material, a heat resistant material, an abrasion resistant material, a sticky material, etc. In addition, the flexible body 96 and protruding portion 98 can be formed in a variety of shapes and sizes, as illustrated in the preferred and non-limiting embodiments of FIGS. 19 and 20. Again, the signal emitting component 100 can be attached to the protruding portion 98 (FIG. 19) or embedded within this protruding portion 98 (FIG. 20).

In one preferred and non-limiting embodiment, the signal emitting member 12 incorporates sealed RFID tags. These tags (signal emitting components 100) can be rated for immersion in liquids and chemicals, and the flexible body 96 and/or the protruding portion 98 may be silicone or rubber over-molded around the sealed signal emitting components 100. Accordingly, the use of such a flexible body 96 and protruding portion 98 helps these portions to act as a "bumper" and to assist in arresting swinging of the second end E2 of the endoscope E.

In addition, these signal emitting members 12 may include a spacer member 99 can be used and incorporated in the body 96. This spacer member 99 provides an offset between the signal emitting component 100 and the item, e.g., an endoscope, which increases the effectiveness of the signal emitting component 100. For example, this spacer member 99 may be formed from a non-metallic, non-reactive material, e.g., silicone, cellulose, ceramic, etc., which assists in separating and insulating the signal emitting component 100 from the item, which may include metal on or in it. When used in connection with an endoscope E, the use of the protruding portion 98 is particularly beneficial, since the endoscope E includes metal parts that normally dramatically degrade the performance of the signal emitting component 100.

Still further, a layer of RF-absorbent material may be placed into the flexible body 96 and/or protruding portion 98 to reduce the impact of any metal embedded in the endoscope E. The use of silicone rubber is useful as it is resistant to the cleaning chemicals, heat, and abrasion. In addition, the stickiness of the flexible body 96 and/or protruding portion 98 assists in keeping the endoscopes E in place, such that they do not slide against each other, which would result in damage to these expensive endoscopes E. Also, the flexible body 96 and/or protruding portion 98 can serve as a structure to reduce the effects of any impact of an endoscope E against the wall 16 of the cabinet 10. Also, and again, the use of such a protruding portion 98 allows the signal emitting component 100 to be physically spaced from the body of the endoscope E, which optimizes reading performance in the overall system.

In a still further preferred and non-limiting embodiment, the signal emitting component 100 (or some signal emitting member 12) can be embedded directly within the endoscope E. For example, if the manufacturer already embeds some identification tag within or on the endoscope E, the presently-invented endoscope tracking system 84 can use this existing tag for tracking/identification purposes. In addition, the location of an embedded tag can be optimized to support use within the system 84 of the present invention.

Figure 21:
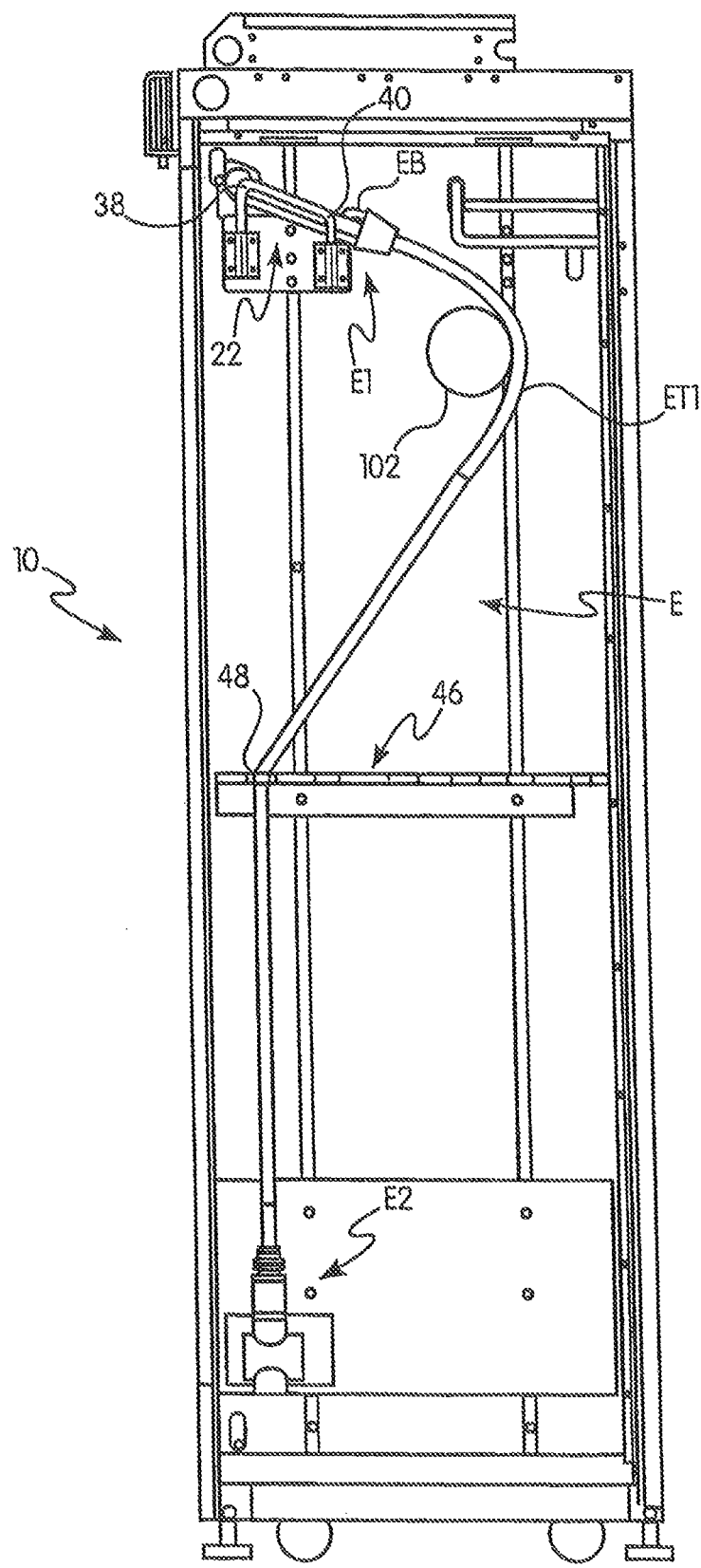
FIG. 21 is a front view of another embodiment of a signal emitting member according to the principles of the present invention.

In a still further preferred and non-limiting embodiment, and as illustrated in FIG. 21, the endoscope E includes an elongated insertion tube ET1 and/or connection tube ET2. These elongated endoscopes E may be utilized for colonoscopies, and the length of at least the insertion tube ET1 may exceed the height of the cabinet 10. Accordingly, such an endoscope E may be stored in a serpentine fashion. Specifically, the main body EB at the first end E1 of the endoscope is positioned on top of the hanger arrangement 22, i.e., resting on the first projecting member 38 and second projecting member 40. This positioning and orientation allows the insertion tube ET1 to extend in an angled (non-vertical) manner, i.e., at a downward slope from one top corner toward the opposite wall of the cabinet 10. An additional bracket 102, formed in such a way as to prevent a sharp bend in the insertion tube ET1 acts as a guide, so that the insertion tube ET1 curves gently around it and back toward the original wall, but still sloping downward. The insertion tube ET1 and/or the connection tube ET2 is then inserted in a hook 48 of the hook arrangement 46 (as discussed above in detail). Such a configuration allows for the storage of these elongated endoscopes E, and the downward slope allows residual moisture to drain from the instrument. In particular, the serpentine curve of the insertion tube ET1 and/or the connection tube ET2 allow the long endoscope E to fit in the height-restricted cabinet 10.

The present invention assists in identifying the nurse and/or clinician who removes an item from the system 84, and issues an alert if an item is out of the storage cabinet 10 after a specified period of time. The cabinets 10 can be locked to allow only authorized and recorded access. Additionally, the system 84 may issue a "dirty scope" alert if placed into a clean cabinet 10, in order to reduce cross contamination. E-mailed messages may be sent to a user's PDA and the challenge screen 78 ensures that if a user U "vouches" for the return of an endoscope E to a cabinet 10, he or she can be associated with a particular endoscope E if it proves "dirty". The present invention can be used to validate other conditions within the overall endoscope tracking system 84, such as conditions or data associated with the reprocessing station 82, disinfection machine 86, etc.

With respect to the alert data 94, the system 84 can assist in providing alerts in real-time to the users U, as well as to issue instructions to the local cabinet 10 to provide some visual alert and/or message at the cabinet 10 location. With respect to patient safety, forced ventilation can be used within the cabinet 10 to dry residual moisture after the washing process. Reports of history and usage, including patients, dates, disinfection, etc., provide additional system improvements, and the closed and secure design of the cabinet 10 protects expensive endoscopes E. In addition, these endoscopes E are protected through the specifically-designed hanger arrangements 22 and hook arrangement 46.

The present invention leads to work force improvement by providing compliance monitoring of both cleaning and disinfection protocols. In addition, time-based measures of work force efficiencies can be tracked. Endoscope E availability is provided in a cross-campus facility manner for indicating exactly where specific endoscopes E are available. Continuous monitoring may identify if a required endoscope E is in reprocessing, in-use, out-for repair, in a specific location, etc.

Still further, an endoscope E can be tracked and associated with a specific surgeon, as well as correlated between individual handlers. Cost can be tracked for the repair of specific endoscopes E, and cumulative costs for the repair of specified endoscopes E (or a group of endoscopes E with a common characteristic) can be provided. For example, the system 84 can be used to track and identify specific characteristics of an identified group of endoscopes E (e.g., a common manufacturer) to determine unique problems associated therewith. Such information and data can be used in improving the overall process, as well as in addressing issues with a specific endoscopes E or groups of endoscopes E at an early stage and in a preventative manner. Further, the presently-invented system 84 allows for the seamless incorporation of "loaner" endoscopes E into the system. In addition, searching functionality is available for tracking when a particular endoscope E should be returned.

As discussed above, alert data 94 may be sent to managers in real-time, and alarm or alert messages delivered directly to the inbox or PDAs of staff or other designated e-distribution locations. Reports indicating actions during reprocessing, endoscope E handling, storage, required regulatory tracking, etc. can be generated, and data analysis used to show patterns related to endoscopes E damaged during processing, or reported damaged, but serviced with no problems found. The system 84 provides recordkeeping associated with high-level disinfection and retention processes, and eliminates the use of paper records. This, in turn, reduces human errors associated with prior art processes, and allows for the monitoring and tracking of technicians and workflows, which can utilize time stamps and other tracking methods to process data.

A cycle counter may be used or incorporated with the system 84 in order to track disinfection steps, as well as cycles since last repair. A cycle count may be automatically displayed at the reprocessing station 82 or some other display device associated with the central control device 88. For example, if an endoscope E is marked for preventative maintenance or service, then washed, the system 84 may warn the user if he or she tries to replace or remove the endoscope E into or from a cabinet 10.

Further advantages provided by the cabinet 10, system 84, and signal emitting member 12 include the ability to apply the signal emitting member 12 in the field, such as at the reprocessing station 82. The use of silicone/rubber over-molded signal emitting members 12 are useful to prevent damage and increase detection capabilities, and certain signal emitting members 12 are useful in conforming to the shape of the light source connector EC or any other portion of the endoscope E based upon the flexible nature of the body 96 and protruding portion 98. When the signal emitting members 12 are applied to the light source connector EC, they are positioned distant from the first end E1 that the surgeon is using, and thus, not in the "way" of the surgeon. Data can be written to and/or stored on the signal emitting component 100, and this information and data provides attributes related to the endoscope E.

As discussed above, any number of signal receiving devices 24 can be used and positioned in any of the areas associated with the enclosed structure 14. As is known, the use of additional antennae 26 may improve detection and the ability to "read" the signal emitting members 12. In addition, the number and configuration of the hanger arrangements 22 can be varied according to the room available in the inner area 20 of the storage cabinet 10. The hanger arrangements 22 can be attached directly to a wall 16 or otherwise through a bracket, e.g., bracket 70. Further, it is envisioned that these hanger arrangements 22 can be removable, and certain holes, recesses, or sleeves, e.g., sleeves 72, provided for allowing the user to configure the cabinet 10 in any desired manner.

In this manner, the present invention provides a storage cabinet 10, an endoscope tracking system 84, and an improved signal emitting member 12 that lead to certain benefits and advantages with respect to known endoscope and general inventory management systems.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A signal emitting member, comprising:
a flexible body configured for attachment to an item; and
a signal emitting component attached to or embedded at least partially within at least a portion of the body and configured to emit a signal therefrom,
wherein the body is in the form of a loop, such that the loop can be stretched and positioned over at least a portion of at least one item, and
wherein the item is at least one of the following: a medical item, a medical device, an endoscope, a light source connector, or any combination thereof.

2. The signal emitting member of claim 1, wherein at least a portion of the signal emitting member is formed from at least one of the following: rubber, silicone, a molded material, a radio frequency absorbent material, a chemical resistant material, a heat resistant material, an abrasion resistant material, a sticky material.

3. The signal emitting member of claim 1, wherein the body comprises a protruding portion, and the signal emitting component is attached to or embedded at least partially within at least a portion of the protruding portion.

4. The signal emitting member of claim 3, further comprising at least one layer of radio frequency-absorbent material positioned on or within at least a portion of the protruding portion of the body.

5. The signal emitting member of claim 1, wherein the signal emitting component comprises at least one radio frequency identification tag.

6. The signal emitting member of claim 1, wherein at least a portion of the body is molded over or around the signal emitting component.

7. The signal emitting member of claim 1, further comprising a spacer member configured to provide an offset between the signal emitting component and at least a portion of the item.

8. The signal emitting member of claim 7, wherein the spacer member at least partially comprises at least one of the following: a non-metallic material, a non-reactive material, silicone, cellulose, ceramic, an insulating material, or any combination thereof.

9. The signal emitting member of claim 1, further comprising at least one layer of radio frequency-absorbent material positioned on or within at least a portion of the body.

10. A signal emitting member, comprising:
a flexible body configured for attachment to an item, the body comprising a protruding portion; and
a signal emitting component attached to or embedded at least partially within at least a portion of the protruding portion and configured to emit a signal therefrom,
wherein the item is at least one of the following: a medical item, a medical device, an endoscope, a light source connector, or any combination thereof.

11. The signal emitting member of claim 10, wherein at least a portion of the signal emitting member is formed from at least one of the following: rubber, silicone, a molded material, a radio frequency absorbent material, a chemical resistant material, a heat resistant material, an abrasion resistant material, a sticky material.

12. The signal emitting member of claim 10, wherein the body is in the form of a loop, such that the loop can be stretched and positioned over at least a portion of at least one item.

13. The signal emitting member of claim 10, wherein the signal emitting component comprises at least one radio frequency identification tag.

14. The signal emitting member of claim 10, wherein at least a portion of the body is molded over or around the signal emitting component.

15. The signal emitting member of claim 10, further comprising a spacer member configured to provide an offset between the signal emitting component and at least a portion of the item.

16. The signal emitting member of claim 15, wherein the spacer member at least partially comprises at least one of the following: a non-metallic material, a non-reactive material, silicone, cellulose, ceramic, an insulating material, or any combination thereof.

17. The signal emitting member of claim 10, further comprising at least one layer of radio frequency-absorbent material positioned on or within at least a portion of the body.

* * * * *